(12) United States Patent
Nguyen et al.

(10) Patent No.: US 10,980,973 B2
(45) Date of Patent: Apr. 20, 2021

(54) DEVICE AND METHOD FOR RELEASING CATHETERS FROM CARDIAC STRUCTURES

(71) Applicant: Ancora Heart, Inc., Santa Clara, CA (US)

(72) Inventors: Huu Nguyen, San Jose, CA (US); Rob Kotmel, Burlingame, CA (US); Tiffany Mirchandani, San Jose, CA (US); Russel Sampson, Palo Alto, CA (US); David Scott Baron, Sunnyvale, CA (US)

(73) Assignee: Ancora Heart, Inc., Santa Clara, CA (US)

( * ) Notice: Subject to any disclaimer, the term of this patent is extended or adjusted under 35 U.S.C. 154(b) by 372 days.

(21) Appl. No.: 15/572,757

(22) PCT Filed: May 12, 2016

(86) PCT No.: PCT/US2016/032220
§ 371 (c)(1),
(2) Date: Nov. 8, 2017

(87) PCT Pub. No.: WO2016/183386
PCT Pub. Date: Nov. 17, 2016

(65) Prior Publication Data
US 2018/0154111 A1 Jun. 7, 2018

Related U.S. Application Data

(60) Provisional application No. 62/160,595, filed on May 12, 2015.

(51) Int. Cl.
*A61M 25/00* (2006.01)
*A61F 2/24* (2006.01)
(Continued)

(52) U.S. Cl.
CPC ..... *A61M 25/0082* (2013.01); *A61B 17/0401* (2013.01); *A61B 17/3468* (2013.01);
(Continued)

(58) Field of Classification Search
CPC ........... A61M 25/0082; A61B 17/0401; A61B 17/3468; A61F 2/2445
See application file for complete search history.

(56) References Cited

U.S. PATENT DOCUMENTS 2,108,206 A  2/1938 Meeker
3,598,576 A  8/1971 Moore et al.
(Continued)

FOREIGN PATENT DOCUMENTS

EP  0 363 661 A1  4/1990
EP  0 669 101 A1  8/1995
(Continued)

OTHER PUBLICATIONS

De Simone, R. et al. (Apr. 1, 1994). "Adjustable Annuloplasty for Tricuspid Insufficiency with External Control," Reader's Comments and Reply, *Am. J. Cardiol.* 73(9):721-722.
(Continued)

*Primary Examiner* — Joseph M Dietrich
(74) *Attorney, Agent, or Firm* — Cooley LLP

(57) ABSTRACT

Devices, systems, and methods for releasing a catheter from an implant may include a catheter comprising first and second elongate elements, first and second elongate element lumens, a tissue anchor lumen, apertures corresponding to each of the lumens, and retaining portions between adjacent apertures. The first elongate element may extend out of its lumen through the first elongate element aperture, across the retaining portion transversely with respect to a longitudinal axis, and towards the second elongate element aperture. The first elongate element may then extend into the second (Continued)

elongate element aperture, loop over the second elongate element, and extend back across the retaining portion and into the first elongate element lumen. In some instances, the second elongate element is retracted to uncouple the first and second elongate elements from each other and to open a channel for the release of tethered tissue anchors.

19 Claims, 19 Drawing Sheets

(51) Int. Cl.
*A61B 17/04* (2006.01)
*A61B 17/34* (2006.01)
*A61B 17/00* (2006.01)
*A61B 17/072* (2006.01)

(52) U.S. Cl.
CPC .......... *A61F 2/2445* (2013.01); *A61F 2/2466* (2013.01); *A61F 2/2487* (2013.01); *A61B 2017/00243* (2013.01); *A61B 2017/00292* (2013.01); *A61B 2017/00309* (2013.01); *A61B 2017/00783* (2013.01); *A61B 2017/0409* (2013.01); *A61B 2017/0417* (2013.01); *A61B 2017/0464* (2013.01); *A61B 2017/07221* (2013.01); *A61M 2025/0096* (2013.01); *A61M 2210/125* (2013.01)

(56) References Cited

U.S. PATENT DOCUMENTS

| | | | |
|---|---|---|---|
| 3,656,185 A | 4/1972 | Carpentier |
| 3,727,614 A | 4/1973 | Kniazuk |
| 3,773,034 A | 11/1973 | Burns et al. |
| 3,961,419 A | 6/1976 | Schwartz |
| 3,976,079 A | 8/1976 | Samuels et al. |
| 4,014,492 A | 3/1977 | Rothfuss |
| 4,034,473 A | 7/1977 | May |
| 4,042,979 A | 8/1977 | Angell |
| 4,043,504 A | 8/1977 | Hueil et al. |
| 4,053,979 A | 10/1977 | Tuthill et al. |
| 4,055,861 A | 11/1977 | Carpentier et al. |
| 4,069,825 A | 1/1978 | Akiyama |
| 4,290,151 A | 9/1981 | Massana |
| 4,384,406 A | 5/1983 | Tischlinger |
| 4,445,892 A | 5/1984 | Hussein et al. |
| 4,489,446 A | 12/1984 | Reed |
| 4,494,542 A | 1/1985 | Lee |
| 4,619,247 A | 10/1986 | Inoue et al. |
| 4,700,250 A | 10/1987 | Kuriyama |
| 4,726,371 A | 2/1988 | Gibbens |
| 4,758,221 A | 7/1988 | Jureidini |
| 4,784,133 A | 11/1988 | Mackin |
| 4,798,594 A | 1/1989 | Hillstead |
| 4,845,851 A | 7/1989 | Warthen |
| 4,848,341 A | 7/1989 | Ahmad |
| 4,850,354 A | 7/1989 | McGurk-Burleson et al. |
| 4,961,738 A | 10/1990 | Mackin |
| 4,969,893 A | 11/1990 | Swor |
| 4,976,710 A | 12/1990 | Mackin |
| 5,053,047 A | 10/1991 | Yoon |
| 5,064,431 A | 11/1991 | Gilbertson et al. |
| 5,078,731 A | 1/1992 | Hayhurst |
| 5,084,058 A | 1/1992 | Li |
| 5,103,804 A | 4/1992 | Abele et al. |
| 5,108,368 A | 4/1992 | Hammerslag et al. |
| 5,133,723 A | 7/1992 | Li et al. |
| 5,221,255 A | 6/1993 | Mahurkar et al. |
| 5,221,269 A | 6/1993 | Miller et al. |
| 5,242,456 A | 9/1993 | Nash et al. |
| 5,242,457 A | 9/1993 | Akopov et al. |
| 5,257,975 A | 11/1993 | Foshee |
| 5,306,296 A | 4/1994 | Wright et al. |
| 5,312,341 A | 5/1994 | Turi |
| 5,324,298 A | 6/1994 | Phillips et al. |
| 5,346,500 A | 9/1994 | Suchart |
| 5,358,479 A | 10/1994 | Wilson |
| 5,358,514 A | 10/1994 | Schulman et al. |
| 5,364,407 A | 11/1994 | Poll |
| 5,366,479 A | 11/1994 | McGarry et al. |
| 5,368,591 A | 11/1994 | Lennox et al. |
| 5,383,905 A | 1/1995 | Golds et al. |
| 5,395,316 A | 3/1995 | Martin |
| 5,409,483 A | 4/1995 | Campbell et al. |
| 5,409,499 A | 4/1995 | Yi |
| 5,417,700 A | 5/1995 | Egan |
| 5,423,837 A | 6/1995 | Mericle et al. |
| 5,437,680 A | 8/1995 | Yoon |
| 5,439,470 A | 8/1995 | Li |
| 5,450,860 A | 9/1995 | O'Connor |
| 5,452,513 A | 9/1995 | Zinnbauer et al. |
| 5,474,572 A | 12/1995 | Hayhurst |
| 5,507,760 A | 4/1996 | Wynne et al. |
| 5,520,702 A | 5/1996 | Sauer et al. |
| 5,522,873 A | 6/1996 | Jackman et al. |
| 5,524,630 A | 6/1996 | Crowley |
| 5,527,323 A | 6/1996 | Jervis et al. |
| 5,531,686 A | 7/1996 | Lundquist et al. |
| 5,545,134 A | 8/1996 | Hilaire et al. |
| 5,545,168 A | 8/1996 | Burke |
| 5,565,122 A | 10/1996 | Zinnbauer et al. |
| 5,571,215 A | 11/1996 | Sterman et al. |
| 5,591,194 A | 1/1997 | Berthiaume |
| 5,626,590 A | 5/1997 | Wilk |
| 5,626,614 A | 5/1997 | Hart |
| 5,630,824 A | 5/1997 | Hart |
| 5,643,289 A | 7/1997 | Sauer et al. |
| 5,669,917 A | 9/1997 | Sauer et al. |
| 5,674,279 A | 10/1997 | Wright et al. |
| 5,690,655 A | 11/1997 | Hart et al. |
| 5,709,695 A | 1/1998 | Northrup, III |
| 5,713,950 A | 2/1998 | Cox |
| 5,716,370 A | 2/1998 | Williamson, IV et al. |
| 5,718,725 A | 2/1998 | Sterman et al. |
| 5,725,542 A | 3/1998 | Yoon |
| 5,735,290 A | 4/1998 | Sterman et al. |
| 5,741,260 A | 4/1998 | Songer et al. |
| 5,741,301 A | 4/1998 | Pagedas |
| 5,752,518 A | 5/1998 | McGee et al. |
| 5,752,964 A | 5/1998 | Mericle |
| 5,752,966 A | 5/1998 | Chang |
| 5,755,730 A | 5/1998 | Swain et al. |
| 5,766,240 A | 6/1998 | Johnson |
| 5,769,812 A | 6/1998 | Stevens et al. |
| 5,782,861 A | 7/1998 | Cragg et al. |
| 5,810,848 A | 9/1998 | Hayhurst |
| 5,810,853 A | 9/1998 | Yoon |
| 5,817,107 A | 10/1998 | Schaller |
| 5,827,171 A | 10/1998 | Dobak, III et al. |
| 5,843,169 A | 12/1998 | Taheri |
| 5,848,969 A | 12/1998 | Panescu et al. |
| 5,860,992 A | 1/1999 | Daniel et al. |
| 5,860,993 A | 1/1999 | Thompson et al. |
| 5,868,733 A | 2/1999 | Ockuly et al. |
| 5,879,371 A | 3/1999 | Gardiner et al. |
| 5,885,238 A | 3/1999 | Stevens et al. |
| 5,888,240 A | 3/1999 | Carpentier et al. |
| 5,902,321 A | 5/1999 | Caspari et al. |
| 5,904,651 A | 5/1999 | Swanson et al. |
| 5,906,579 A | 5/1999 | Vander Salm et al. |
| 5,911,717 A | 6/1999 | Jacobsen et al. |
| 5,919,207 A | 7/1999 | Taheri |
| 5,919,208 A | 7/1999 | Valenti |
| 5,935,149 A | 8/1999 | Ek |
| 5,947,983 A | 9/1999 | Solar et al. |
| 5,961,440 A | 10/1999 | Schweich, Jr. et al. |
| 5,961,539 A | 10/1999 | Northrup, III et al. |
| 5,972,004 A | 10/1999 | Williamson, IV et al. |
| 5,984,933 A | 11/1999 | Yoon |
| 5,989,284 A | 11/1999 | Laufer |
| 5,991,650 A | 11/1999 | Swanson et al. |
| 6,010,531 A | 1/2000 | Donlon et al. |

(56) References Cited

U.S. PATENT DOCUMENTS

| | | |
|---|---|---|
| 6,015,428 A | 1/2000 | Pagedas |
| 6,045,497 A | 4/2000 | Schweich, Jr. |
| 6,050,936 A | 4/2000 | Schweich, Jr. et al. |
| 6,056,743 A | 5/2000 | Ellis et al. |
| 6,059,715 A | 5/2000 | Schweich, Jr. et al. |
| 6,066,160 A | 5/2000 | Colvin et al. |
| 6,074,401 A | 6/2000 | Gardiner et al. |
| 6,077,214 A | 6/2000 | Mortier et al. |
| 6,077,989 A | 6/2000 | Kandel et al. |
| 6,099,553 A | 8/2000 | Hart et al. |
| 6,102,945 A | 8/2000 | Campbell |
| 6,125,852 A | 10/2000 | Stevens et al. |
| 6,149,658 A | 11/2000 | Gardiner et al. |
| 6,162,168 A | 12/2000 | Schweich, Jr. et al. |
| 6,165,183 A | 12/2000 | Kuehn et al. |
| 6,171,329 B1 | 1/2001 | Shaw et al. |
| 6,183,469 B1 | 2/2001 | Thapliyal et al. |
| 6,197,017 B1 | 3/2001 | Brock et al. |
| 6,203,531 B1 | 3/2001 | Ockuly et al. |
| 6,221,084 B1 | 4/2001 | Fleenor |
| 6,228,055 B1 | 5/2001 | Foerster et al. |
| 6,228,096 B1 | 5/2001 | Marchand |
| 6,250,308 B1 | 6/2001 | Cox |
| 6,254,620 B1 | 7/2001 | Koh et al. |
| 6,258,118 B1 | 7/2001 | Baum et al. |
| 6,260,552 B1 | 7/2001 | Mortier et al. |
| 6,269,819 B1 | 8/2001 | Oz et al. |
| 6,283,993 B1 | 9/2001 | Cosgrove et al. |
| 6,306,149 B1 | 10/2001 | Meade |
| 6,312,447 B1 | 11/2001 | Grimes |
| 6,328,727 B1 | 12/2001 | Frazier et al. |
| 6,332,893 B1 | 12/2001 | Mortier et al. |
| 6,355,030 B1 | 3/2002 | Aldrich et al. |
| 6,378,289 B1 | 4/2002 | Trudeau et al. |
| 6,391,048 B1 | 5/2002 | Ginn et al. |
| 6,406,420 B1 | 6/2002 | McCarthy et al. |
| 6,409,743 B1 | 6/2002 | Fenton, Jr. |
| 6,423,088 B1 | 7/2002 | Fenton, Jr. |
| 6,432,123 B2 | 8/2002 | Schwartz et al. |
| 6,461,327 B1 | 10/2002 | Addis et al. |
| 6,491,689 B1 | 12/2002 | Ellis et al. |
| 6,514,265 B2 | 2/2003 | Ho et al. |
| 6,524,328 B2 | 2/2003 | Levinson |
| 6,524,338 B1 | 2/2003 | Gundry |
| 6,533,753 B1 | 3/2003 | Haarstad et al. |
| 6,551,332 B1 | 4/2003 | Nguyen et al. |
| 6,575,971 B2 | 6/2003 | Hauck et al. |
| 6,575,987 B2 | 6/2003 | Gellman et al. |
| 6,589,160 B2 | 7/2003 | Schweich, Jr. et al. |
| 6,602,288 B1 | 8/2003 | Cosgrove et al. |
| 6,602,289 B1 | 8/2003 | Colvin et al. |
| 6,607,541 B1 | 8/2003 | Gardiner et al. |
| 6,613,059 B2 | 9/2003 | Schaller et al. |
| 6,619,291 B1 | 9/2003 | Hlavka et al. |
| 6,626,899 B2 | 9/2003 | Houser et al. |
| 6,629,534 B1 | 10/2003 | St. Goar et al. |
| 6,641,593 B1 | 11/2003 | Schaller et al. |
| 6,648,903 B1 | 11/2003 | Pierson, III |
| 6,651,671 B1 | 11/2003 | Donlon et al. |
| 6,655,386 B1 | 12/2003 | Makower et al. |
| 6,669,687 B1 | 12/2003 | Saadat |
| 6,676,702 B2 | 1/2004 | Mathis |
| 6,689,164 B1 | 2/2004 | Seguin |
| 6,699,263 B2 | 3/2004 | Cope |
| 6,702,826 B2 | 3/2004 | Liddicoat et al. |
| 6,716,243 B1 | 4/2004 | Colvin et al. |
| 6,718,985 B2 | 4/2004 | Hlavka et al. |
| 6,723,038 B1 | 4/2004 | Schoeder et al. |
| 6,723,107 B1 | 4/2004 | Skiba et al. |
| 6,733,509 B2 | 5/2004 | Nobles et al. |
| 6,746,457 B2 | 6/2004 | Dana et al. |
| 6,749,622 B2 | 6/2004 | McGuckin et al. |
| 6,752,813 B2 | 6/2004 | Goldfarb et al. |
| 6,790,231 B2 | 9/2004 | Liddicoat et al. |
| 6,793,618 B2 | 9/2004 | Schweich, Jr. et al. |
| 6,802,851 B2 | 10/2004 | Jones et al. |
| 6,811,560 B2 | 11/2004 | Jones et al. |
| 6,818,001 B2 | 11/2004 | Wulfman et al. |
| 6,875,224 B2 | 4/2005 | Grimes |
| 6,908,424 B2 | 6/2005 | Mortier et al. |
| 6,923,818 B2 | 8/2005 | Muramatsu et al. |
| 6,932,792 B1 | 8/2005 | St. Goar et al. |
| 6,951,557 B2 | 10/2005 | Ellis et al. |
| 6,986,775 B2 | 1/2006 | Morales et al. |
| 6,991,643 B2 | 1/2006 | Saadat |
| 6,997,931 B2 | 2/2006 | Sauer et al. |
| 7,004,958 B2 | 2/2006 | Adams et al. |
| 7,037,334 B1 | 5/2006 | Hlavka et al. |
| 7,044,957 B2 | 5/2006 | Foerster et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,166,127 B2 | 1/2007 | Spence et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,235,086 B2 | 6/2007 | Sauer et al. |
| 7,241,310 B2 | 7/2007 | Taylor et al. |
| 7,326,231 B2 | 2/2008 | Phillips et al. |
| 7,335,213 B1 | 2/2008 | Hyde et al. |
| 7,344,544 B2 | 3/2008 | Bender et al. |
| 7,452,325 B2 | 11/2008 | Schaller |
| 7,534,204 B2 | 5/2009 | Starksen et al. |
| 7,588,582 B2 | 9/2009 | Starksen et al. |
| 7,618,449 B2 | 11/2009 | Tremulis et al. |
| 7,655,040 B2 | 2/2010 | Douk et al. |
| 7,666,193 B2 | 2/2010 | Starksen et al. |
| 7,727,247 B2 | 6/2010 | Kimura et al. |
| 7,753,858 B2 | 7/2010 | Starksen et al. |
| 7,753,922 B2 | 7/2010 | Starksen |
| 7,753,924 B2 | 7/2010 | Starksen et al. |
| 7,758,637 B2 | 7/2010 | Starksen et al. |
| 7,766,812 B2 | 8/2010 | Schroeder et al. |
| 7,832,406 B2 | 11/2010 | Ellis et al. |
| 7,850,600 B1 | 12/2010 | Piskun |
| 7,883,538 B2 | 2/2011 | To et al. |
| 7,918,787 B2 | 4/2011 | Saadat |
| 7,922,762 B2 | 4/2011 | Starksen |
| 7,993,368 B2 | 8/2011 | Gambale et al. |
| 8,066,766 B2 | 11/2011 | To et al. |
| 8,287,555 B2 | 10/2012 | Starksen et al. |
| 8,287,557 B2 | 10/2012 | To et al. |
| 8,343,173 B2 | 1/2013 | Starksen et al. |
| 8,641,727 B2 | 2/2014 | Starksen et al. |
| 8,790,367 B2 | 7/2014 | Nguyen et al. |
| 9,072,513 B2 | 7/2015 | To et al. |
| 9,226,825 B2 | 1/2016 | Starksen et al. |
| 9,468,528 B2 | 10/2016 | Starksen et al. |
| 9,706,996 B2 | 7/2017 | Nguyen et al. |
| 9,949,829 B2 | 4/2018 | Starksen et al. |
| 10,092,402 B2 | 10/2018 | Starksen et al. |
| 10,542,987 B2 | 1/2020 | Nguyen et al. |
| 10,624,741 B2 | 4/2020 | Starksen et al. |
| 2001/0005787 A1 | 6/2001 | Oz et al. |
| 2001/0014800 A1 | 8/2001 | Frazier et al. |
| 2001/0023332 A1 | 9/2001 | Hahnen |
| 2001/0031979 A1 | 10/2001 | Ricci |
| 2001/0034528 A1 | 10/2001 | Foerster et al. |
| 2001/0041821 A1 | 11/2001 | Wilk |
| 2002/0013571 A1 | 1/2002 | Goldfarb et al. |
| 2002/0013621 A1 | 1/2002 | Stobie et al. |
| 2002/0026201 A1 | 2/2002 | Foerster et al. |
| 2002/0029080 A1 | 3/2002 | Mortier et al. |
| 2002/0035361 A1 | 3/2002 | Houser et al. |
| 2002/0042621 A1 | 4/2002 | Liddicoat et al. |
| 2002/0065536 A1 | 5/2002 | Hart et al. |
| 2002/0072757 A1 | 6/2002 | Ahmed et al. |
| 2002/0077524 A1 | 6/2002 | Schweich, Jr. et al. |
| 2002/0087048 A1 | 7/2002 | Brock et al. |
| 2002/0087049 A1 | 7/2002 | Brock et al. |
| 2002/0087148 A1 | 7/2002 | Brock et al. |
| 2002/0087169 A1 | 7/2002 | Brock et al. |
| 2002/0095167 A1 | 7/2002 | Liddicoat et al. |
| 2002/0095175 A1 | 7/2002 | Brock et al. |

(56) References Cited

U.S. PATENT DOCUMENTS

| | | |
|---|---|---|
| 2002/0138044 A1 | 9/2002 | Streeter et al. |
| 2002/0156526 A1 | 10/2002 | Hlavka et al. |
| 2002/0161378 A1 | 10/2002 | Downing |
| 2002/0165486 A1 | 11/2002 | Bertolero et al. |
| 2002/0165561 A1 | 11/2002 | Ainsworth et al. |
| 2002/0173841 A1 | 11/2002 | Ortiz et al. |
| 2002/0183787 A1 | 12/2002 | Wahr et al. |
| 2002/0183835 A1 | 12/2002 | Taylor et al. |
| 2002/0193815 A1 | 12/2002 | Foerster et al. |
| 2003/0009196 A1 | 1/2003 | Peterson |
| 2003/0014060 A1 | 1/2003 | Wilson |
| 2003/0018358 A1 | 1/2003 | Saadat |
| 2003/0032979 A1 | 2/2003 | Mortier et al. |
| 2003/0033006 A1 | 2/2003 | Phillips et al. |
| 2003/0060813 A1 | 3/2003 | Loeb et al. |
| 2003/0069593 A1 | 4/2003 | Tremulis et al. |
| 2003/0074012 A1 | 4/2003 | Nguyen et al. |
| 2003/0078465 A1 | 4/2003 | Pai et al. |
| 2003/0078601 A1 | 4/2003 | Shikhman et al. |
| 2003/0078603 A1 | 4/2003 | Schaller et al. |
| 2003/0093118 A1 | 5/2003 | Ho et al. |
| 2003/0105520 A1 | 6/2003 | Alferness et al. |
| 2003/0125739 A1 | 7/2003 | Bagga et al. |
| 2003/0125767 A1 | 7/2003 | Collier et al. |
| 2003/0130731 A1 | 7/2003 | Vidlund et al. |
| 2003/0144697 A1 | 7/2003 | Mathis et al. |
| 2003/0158464 A1 | 8/2003 | Bertolero |
| 2003/0158581 A1 | 8/2003 | Levinson |
| 2003/0167062 A1 | 9/2003 | Gambale et al. |
| 2003/0167071 A1 | 9/2003 | Martin et al. |
| 2003/0199974 A1 | 10/2003 | Lee et al. |
| 2003/0220685 A1 | 11/2003 | Hlvaka et al. |
| 2003/0225420 A1 | 12/2003 | Wardle |
| 2003/0233105 A1 | 12/2003 | Gayton |
| 2003/0233142 A1 | 12/2003 | Morales et al. |
| 2003/0236535 A1 | 12/2003 | Onuki et al. |
| 2004/0003819 A1 | 1/2004 | St. Goar et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0092962 A1 | 5/2004 | Thornton et al. |
| 2004/0093024 A1 | 5/2004 | Lousararian et al. |
| 2004/0097788 A1 | 5/2004 | Mourlas et al. |
| 2004/0122450 A1 | 6/2004 | Oren et al. |
| 2004/0152947 A1 | 8/2004 | Schroeder et al. |
| 2004/0162465 A1 | 8/2004 | Carrillo |
| 2004/0172046 A1 | 9/2004 | Hlavka et al. |
| 2004/0181238 A1 | 9/2004 | Zarbatany et al. |
| 2004/0186378 A1 | 9/2004 | Gesswein |
| 2004/0193191 A1 | 9/2004 | Starksen et al. |
| 2004/0204724 A1 | 10/2004 | Kissel et al. |
| 2004/0210238 A1 | 10/2004 | Nobles et al. |
| 2004/0236372 A1 | 11/2004 | Anspach, III et al. |
| 2004/0236419 A1 | 11/2004 | Milo |
| 2004/0243227 A1 | 12/2004 | Starksen et al. |
| 2005/0021054 A1 | 1/2005 | Ainsworth et al. |
| 2005/0055052 A1 | 3/2005 | Lombardo et al. |
| 2005/0055087 A1 | 3/2005 | Starksen |
| 2005/0065550 A1 | 3/2005 | Starksen et al. |
| 2005/0065589 A1 | 3/2005 | Schneider et al. |
| 2005/0075723 A1 | 4/2005 | Schroeder et al. |
| 2005/0080454 A1 | 4/2005 | Drews et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0119523 A1 | 6/2005 | Starksen et al. |
| 2005/0119673 A1 | 6/2005 | Gordon et al. |
| 2005/0137689 A1 | 6/2005 | Salahieh et al. |
| 2005/0177180 A1 | 8/2005 | Kaganov et al. |
| 2005/0184122 A1 | 8/2005 | Hlavka et al. |
| 2005/0192599 A1 | 9/2005 | Demarais |
| 2005/0192629 A1 | 9/2005 | Saadat et al. |
| 2005/0197694 A1 | 9/2005 | Pai et al. |
| 2005/0209690 A1 | 9/2005 | Mathis et al. |
| 2005/0216078 A1 | 9/2005 | Starksen et al. |
| 2005/0228452 A1 | 10/2005 | Mourlas et al. |
| 2005/0251157 A1 | 11/2005 | Saadat et al. |
| 2005/0251159 A1 | 11/2005 | Ewers et al. |
| 2005/0251166 A1 | 11/2005 | Vaughan et al. |
| 2005/0251177 A1 | 11/2005 | Saadat et al. |
| 2005/0251205 A1 | 11/2005 | Ewers et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267495 A1 | 12/2005 | Ginn et al. |
| 2005/0273138 A1 | 12/2005 | To et al. |
| 2005/0277966 A1 | 12/2005 | Ewers et al. |
| 2005/0277981 A1 | 12/2005 | Maahs et al. |
| 2005/0277983 A1 | 12/2005 | Saadat et al. |
| 2006/0015144 A1 | 1/2006 | Burbank et al. |
| 2006/0025750 A1 | 2/2006 | Starksen et al. |
| 2006/0025784 A1 | 2/2006 | Starksen et al. |
| 2006/0025787 A1 | 2/2006 | Morales et al. |
| 2006/0058817 A1 | 3/2006 | Starksen et al. |
| 2006/0069429 A1 | 3/2006 | Spence et al. |
| 2006/0122633 A1 | 6/2006 | To et al. |
| 2006/0129188 A1 | 6/2006 | Starksen et al. |
| 2006/0161040 A1 | 7/2006 | McCarthy et al. |
| 2006/0178682 A1 | 8/2006 | Boehlke |
| 2006/0184203 A1 | 8/2006 | Martin et al. |
| 2006/0190030 A1 | 8/2006 | To et al. |
| 2006/0241656 A1 | 10/2006 | Starksen et al. |
| 2006/0264975 A1 | 11/2006 | Pipenhagen et al. |
| 2006/0271101 A1 | 11/2006 | Saadat et al. |
| 2006/0282161 A1 | 12/2006 | Huynh et al. |
| 2006/0287661 A1 | 12/2006 | Bolduc et al. |
| 2007/0005081 A1 | 1/2007 | Findlay, III et al. |
| 2007/0005394 A1 | 1/2007 | Bleyendaal et al. |
| 2007/0010857 A1 | 1/2007 | Sugimoto et al. |
| 2007/0032820 A1 | 2/2007 | Chin-Chen et al. |
| 2007/0038293 A1 | 2/2007 | St. Goar et al. |
| 2007/0049942 A1 | 3/2007 | Hindrichs et al. |
| 2007/0051377 A1 | 3/2007 | Douk et al. |
| 2007/0055206 A1 | 3/2007 | To et al. |
| 2007/0112244 A1 | 5/2007 | McCarthy et al. |
| 2007/0112422 A1 | 5/2007 | Dehdashtian |
| 2007/0112424 A1 | 5/2007 | Spence et al. |
| 2007/0112425 A1 | 5/2007 | Schaller |
| 2008/0045977 A1 | 2/2008 | To et al. |
| 2008/0045982 A1 | 2/2008 | To et al. |
| 2008/0045983 A1 | 2/2008 | To et al. |
| 2008/0051810 A1 | 2/2008 | To et al. |
| 2008/0051832 A1 | 2/2008 | To et al. |
| 2008/0051837 A1 | 2/2008 | To et al. |
| 2008/0058765 A1 | 3/2008 | Jais et al. |
| 2008/0058868 A1 | 3/2008 | To et al. |
| 2008/0172035 A1 | 7/2008 | Starksen et al. |
| 2008/0177380 A1 | 7/2008 | Starksen et al. |
| 2008/0228032 A1 | 9/2008 | Starksen et al. |
| 2008/0234701 A1 | 9/2008 | Morales et al. |
| 2008/0234702 A1 | 9/2008 | Morales et al. |
| 2008/0234704 A1 | 9/2008 | Starksen et al. |
| 2008/0234728 A1 | 9/2008 | Starksen et al. |
| 2008/0234815 A1 | 9/2008 | Starksen |
| 2008/0243150 A1 | 10/2008 | Starksen et al. |
| 2008/0294177 A1 | 11/2008 | To et al. |
| 2008/0312712 A1 | 12/2008 | Penner |
| 2009/0054824 A1 | 2/2009 | Melsheimer |
| 2009/0182417 A1 | 7/2009 | Tremulis et al. |
| 2009/0222083 A1 | 9/2009 | Nguyen et al. |
| 2009/0234318 A1 | 9/2009 | Loulmet et al. |
| 2009/0276038 A1 | 11/2009 | Tremulis et al. |
| 2010/0049213 A1 | 2/2010 | Serina et al. |
| 2010/0076548 A1 | 3/2010 | Konno |
| 2010/0082098 A1 | 4/2010 | Starksen et al. |
| 2010/0094248 A1 | 4/2010 | Nguyen et al. |
| 2010/0094314 A1 | 4/2010 | Hernlund et al. |
| 2010/0121349 A1 | 5/2010 | Meier et al. |
| 2011/0160528 A1 | 6/2011 | Starksen |
| 2012/0101442 A1 | 4/2012 | Legaspi et al. |
| 2012/0271331 A1 | 10/2012 | To et al. |

(56) References Cited

U.S. PATENT DOCUMENTS

| | | |
|---|---|---|
| 2013/0304093 A1 | 11/2013 | Serina et al. |
| 2014/0135799 A1 | 5/2014 | Henderson |
| 2014/0148849 A1 | 5/2014 | Eugene et al. |
| 2014/0155783 A1 | 6/2014 | Starksen et al. |
| 2014/0188140 A1 | 7/2014 | Meier et al. |
| 2014/0303649 A1 | 10/2014 | Nguyen et al. |
| 2015/0164639 A1 | 6/2015 | Starksen et al. |
| 2015/0182216 A1 | 7/2015 | Morales et al. |
| 2017/0224489 A1 | 8/2017 | Starksen et al. |
| 2018/0153553 A1 | 6/2018 | Nguyen et al. |
| 2018/0154111 A1 | 6/2018 | Nguyen et al. |
| 2019/0091023 A1 | 3/2019 | Starksen et al. |
| 2020/0229820 A1 | 7/2020 | Nguyen et al. |

FOREIGN PATENT DOCUMENTS

| | | |
|---|---|---|
| GB | 1370546 A | 10/1974 |
| JP | 6-510460 A | 11/1994 |
| JP | 11-506628 A | 6/1999 |
| JP | 2004-601 A | 1/2004 |
| JP | 2007-514455 A | 6/2007 |
| JP | 48-23295 B2 | 11/2011 |
| WO | WO-93/08740 A1 | 5/1993 |
| WO | WO-94/03227 A1 | 2/1994 |
| WO | WO-95/15715 A1 | 6/1995 |
| WO | WO-96/08208 A1 | 3/1996 |
| WO | WO-96/39081 A1 | 6/1996 |
| WO | WO-96/39942 A1 | 12/1996 |
| WO | WO-97/27799 A1 | 8/1997 |
| WO | WO-97/27807 A1 | 8/1997 |
| WO | WO-97/30639 A1 | 8/1997 |
| WO | WO-98/07375 A1 | 2/1998 |
| WO | WO-02/053011 A3 | 7/2000 |
| WO | WO-00/60995 A2 | 10/2000 |
| WO | WO-00/60995 A3 | 10/2000 |
| WO | WO-00/67640 A2 | 11/2000 |
| WO | WO-00/67640 A3 | 11/2000 |
| WO | WO-01/26586 A1 | 4/2001 |
| WO | WO-01/54618 A1 | 8/2001 |
| WO | WO-02/03892 A1 | 1/2002 |
| WO | WO-02/034167 A2 | 5/2002 |
| WO | WO-02/034167 A3 | 5/2002 |
| WO | WO-02/051329 A1 | 7/2002 |
| WO | WO-02/053011 A2 | 7/2002 |
| WO | WO-02/085251 A1 | 10/2002 |
| WO | WO-02/085252 A1 | 10/2002 |
| WO | WO-03/088875 A1 | 10/2003 |
| WO | WO-03/105667 A2 | 12/2003 |
| WO | WO-03/105667 A3 | 12/2003 |
| WO | WO-03/105670 A2 | 12/2003 |
| WO | WO-03/105670 A3 | 12/2003 |
| WO | WO-2004/037317 A2 | 5/2004 |
| WO | WO-2004/037317 A3 | 5/2004 |
| WO | WO-2004/082523 A2 | 9/2004 |
| WO | WO-2004/082523 A3 | 9/2004 |
| WO | WO-2004/082538 A2 | 9/2004 |
| WO | WO-2004/082538 A3 | 9/2004 |
| WO | WO-2005/025644 A2 | 3/2005 |
| WO | WO-2005/025644 A3 | 3/2005 |
| WO | WO-2005/062931 A2 | 7/2005 |
| WO | WO-2005/062931 A3 | 7/2005 |
| WO | WO-2005/102181 A1 | 11/2005 |
| WO | WO-2006/037073 A2 | 4/2006 |
| WO | WO-2006/037073 A3 | 4/2006 |
| WO | WO-2006/097931 A2 | 9/2006 |
| WO | WO-2006/097931 A3 | 9/2006 |
| WO | WO-2006/116558 A2 | 11/2006 |
| WO | WO-2006/116558 A3 | 11/2006 |
| WO | WO-2007/001936 A2 | 1/2007 |
| WO | WO-2007/001936 A3 | 1/2007 |
| WO | WO-2007/005495 A1 | 1/2007 |
| WO | WO-2007/021564 A1 | 2/2007 |
| WO | WO-2007/021834 A1 | 2/2007 |
| WO | WO-2007/035449 A2 | 3/2007 |
| WO | WO-2007/035449 A3 | 3/2007 |
| WO | WO-2007/056502 A1 | 5/2007 |
| WO | WO-2007/100409 A2 | 9/2007 |
| WO | WO-2007/100409 A3 | 9/2007 |
| WO | WO-2008/028135 A2 | 3/2008 |
| WO | WO-2008/028135 A3 | 3/2008 |
| WO | WO-2009/100242 A2 | 8/2009 |
| WO | WO-2009/100242 A3 | 8/2009 |
| WO | WO-2012/031204 | 3/2012 |

OTHER PUBLICATIONS

De Simone, R. et al. (Apr. 15, 1993). "Adjustable Tricuspid Valve Annuloplasty Assisted by Intraoperative Transesophageal Color Doppler Echocardiography," *Am. J. Cardiol.* 71(11):926-931.

Downing, S.W. et al. (2002). "Feasibility of Off-Pump ASD Closure Using Real-Time 3-D Echocardiography," *The Heart Surgery Forum* 5(2):96-99, Abstract 7025.

European Examination Communication dated Dec. 8, 2009, for EP Application No. 06 837 222.6 filed on Nov. 8, 2006, 3 pages.

Extended European Search Report dated Sep. 16, 2011, for EP Patent Application No. 11158898.4, filed on Sep. 1, 2004, 8 pages.

Extended European Search Report dated Sep. 9, 2011, for EP Patent Application No. 11158896.8, filed on Sep. 1, 2004, 7 pages.

Final Office Action dated Apr. 10, 2009, for U.S. Appl. No. 11/255,400, filed Oct. 20, 2005, 8 pages.

Final Office Action dated Apr. 10, 2009, for U.S. Appl. No. 11/414,657, filed Apr. 27, 2006, 8 pages.

Final Office Action dated Apr. 14, 2008, for U.S. Appl. No. 10/901,019, filed Jul. 27, 2004, 11 pages.

Final Office Action dated Apr. 15, 2016, for U.S. Appl. No. 14/309,837, filed Jun. 19, 2014, 5 pages.

Final Office Action dated Apr. 2, 2008, for U.S. Appl. No. 10/792,681, filed Mar. 2, 2004, 15 pages.

Final Office Action dated Apr. 20, 2011, for U.S. Appl. No. 11/414,657, filed Apr. 27, 2006, 8 pages.

Final Office Action dated Apr. 29, 2009, for U.S. Appl. No. 10/901,019, filed Jul. 27, 2004, 9 pages.

Final Office Action dated Aug. 1, 2008, for U.S. Appli. No. 11/232,190, filed Sep. 20, 2005, 8 pages.

Final Office Action dated Aug. 13, 2007, for U.S. Appl. No. 10/900,980, filed Jul. 27, 2004, 9 pages.

Final Office Action dated Aug. 14, 2007, for U.S. Appl. No. 11/255,400, filed Oct. 20, 2005, 8 pages.

Final Office Action dated Aug. 30, 2007, for U.S. Appl. No. 11/232,190, filed Sep. 20, 2005, 9 pages.

Final Office Action dated Aug. 4, 2011, for U.S. Appl. No. 10/900,980, filed Jul. 27, 2004, 9 pages.

Final Office Action dated Aug. 6, 2007, for U.S. Appl. No. 10/901,019, filed Jul. 27, 2004, 12 pages.

Final Office Action dated Aug. 6, 2007, for U.S. Appl. No. 11/137,833, filed May 24, 2005, 8 pages.

Final Office Action dated Dec. 6, 2011, for U.S. Appl. No. 12/366,553, filed Feb. 5, 2009, 7 pages.

Final Office Action dated Feb. 24, 2011, for U.S. Appl. No. 11/894,397, filed Aug. 20, 2007, 12 pages.

Final Office Action dated Feb. 24, 2011, for U.S. Appl. No. 11/894,468, filed Aug. 20, 2007, 12 pages.

Final Office Action dated Feb. 4, 2016, for U.S. Appl. No. 14/626,826, filed Feb. 19, 2015, 9 pages.

Final Office Action dated Feb. 5, 2015, for U.S. Appl. No. 13/540,499, filed Jul. 2, 2012, 10 pages.

Final Office Action dated Feb. 6, 2007, for U.S. Appl. No. 10/656,797, filed Sep. 4, 2003, 8 pages.

Final Office Action dated Jan. 22, 2009, for U.S. Appl. No. 11/255,400, filed Oct. 20, 2005, 9 pages.

Final Office Action dated Jul. 12, 2007, for U.S. Appl. No. 11/202,474, filed Aug. 11, 2005, 10 pages.

Final Office Action dated Jul. 21, 2009, for U.S. Appl. No. 11/270,034, filed Nov. 8, 2005, 8 pages.

Final Office Action dated Jul. 24, 2007, for U.S. Appl. No. 10/741,130, filed Dec. 19, 2003, 10 pages.

Final Office Action dated Jul. 26, 2010, for U.S. Appl. No. 11/270,034, filed Nov. 8, 2005, 8 pages.

(56) References Cited

OTHER PUBLICATIONS

Final Office Action dated Jun. 11, 2012, for U.S. Appl. No. 12/132,161, filed Jun. 3, 2008, 13 pages.
Final Office Action dated Jun. 11, 2012, for U.S. Appl. No. 12/187,331, filed Aug. 6, 2008, 7 pages.
Final Office Action dated Jun. 4, 2008, for U.S. Appl. No. 11/202,474, filed Aug. 11, 2005, 10 pages.
Final Office Action dated Jun. 8, 2010, for U.S. Appl. No. 10/792,681, filed Mar. 2, 2004, 17 pages.
Final Office Action dated Mar. 11, 2009, for U.S. Appl. No. 10/656,797, filed Sep. 4, 2003, 10 pages.
Final Office Action dated Mar. 17, 2011, for U.S. Appl. No. 10/901,554, filed Jul. 27, 2004, 13 pages.
Final Office Action dated Mar. 17, 2011, for U.S. Appl. No. 11/202,474, filed Aug. 11, 2005, 9 pages.
Final Office Action dated Mar. 19, 2012, for U.S. Appl. No. 12/574,563, filed Oct. 6, 2009, 6 pages.
Final Office Action dated Mar. 25, 2010, for U.S. Appl. No. 10/900,980, filed Jul. 27, 2004, 8 pages.
Final Office Action dated Mar. 3, 2010, for U.S. Appl. No. 11/414,657, filed Apr. 27, 2006, 7 pages.
Final Office Action dated May 28, 2008, for U.S. Appl. No. 11/270,034, filed Nov. 8, 2005, 10 pages.
Final Office Action dated Nov. 10, 2009, for U.S. Appl. No. 10/741,130, filed Dec. 19, 2003, 9 pages.
Final Office Action dated Nov. 10, 2011, for U.S. Appl. No. 10/792,681, filed Mar. 2, 2004, 20 pages.
Final Office Action dated Nov. 26, 2010, for U.S. Appl. No. 11/894,340, filed Aug. 20, 2007, 12 pages.
Final Office Action dated Nov. 29, 2010, for U.S. Appl. No. 11/894,463, filed Aug. 20, 2007, 12 pages.
Final Office Action dated Nov. 3, 2017, for U.S. Appl. No. 13/540,499, filed Jul. 2, 2012, 10 pages.
Final Office Action dated Oct. 13, 2009, for U.S. Appl. No. 10/901,554, filed Jul. 27, 2004, 11 pages.
Final Office Action dated Oct. 14, 2008, for U.S. Appl. No. 10/741,130, filed Dec. 19, 2003, 9 pages.
Final Office Action dated Oct. 30, 2007, for U.S. Appl. No. 10/656,797, filed Sep. 4, 2003, 6 pages.
Final Office Action dated Oct. 6, 2010, for U.S. Appl. No. 12/132,375, filed Jun. 3, 2008, 9 pages.
Final Office Action dated Sep. 14, 2017, for U.S. Appl. No. 14/626,826, filed Feb. 19, 2015, 8 pages.
Final Office Action dated Sep. 15, 2010, for U.S. Appl. No. 11/894,401, filed Aug. 20, 2007, 6 pages.
Final Office Action dated Sep. 2, 2009, for U.S. Appl. No. 11/232,190, filed Sep. 20, 2005, 8 pages.
Final Office Action dated Sep. 28, 2009, for U.S. Appl. No. 11/202,474, filed Aug. 11, 2005, 10 pages.
Final Office Action dated Sep. 30, 2008, for U.S. Appl. No. 10/900,980, filed Jul. 27, 2004, 7 pages.
Final Office Action dated Jun. 11, 2012, for U.S. Appl. No. 14/626,826, filed Feb. 19 2015, 7 pages.
International Search Report dated Nov. 17, 2016 in PCT Application No. PCT/US2016/032220 filed May 12, 2016. 2 pages.
International Search Report dated Dec. 19, 2006, for PCT Application No. PCT/US2006/031190, filed Aug. 10, 2006, 4 pages.
International Search Report dated Apr. 2, 2007, for PCT Application No. PCT/US2006/043597, filed Nov. 8, 2006, 4 pages.
International Search Report dated Mar. 7, 2007, for PCT Patent Application No. PCT/US2004/028431, filed on Sep. 1, 2004, 1 page.
International Search Report dated Sep. 15, 2009, for PCT Patent Application No. PCT/US2009/033252, filed on Feb. 5, 2009, 1 page.
Nagy, Z.L. et al. (Dec. 2000). "Mitral Annuloplasty with a Suture Technique," *European Journal of Cardio-thoracic Surgery* 18(6):739-740.
Non-Final Office Action (Supplementary) dated May 9, 2008, for U.S. Appl. No. 11/255,400, filed Oct. 20, 2005, 7 pages.

Non-Final Office Action dated Apr. 2, 2010, for U.S. Appl. No. 12/132,375, filed Jun. 3, 2008, 9 pages.
Non-Final Office Action dated Apr. 21, 2016, for U.S. Appl. No. 13/540,499, filed Jul. 2, 2012, 13 pages.
Non-Final Office Action dated Apr. 27, 2011, for U.S. Appl. No. 12/366,553, filed Feb. 5, 2009, 9 pages.
Non-Final Office Action dated Apr. 8, 2013, for U.S. Appl. No. 11/414,657, filed Apr. 27, 2006, 9 pages.
Non-Final Office Action dated Aug. 1, 2007, for U.S. Appl. No. 10/792,681, filed Mar. 2, 2004, 16 pages.
Non-Final Office Action dated Aug. 17, 2010, for U.S. Appl. No. 11/414,657, filed Apr. 27, 2006, 7 pages.
Non-Final Office Action dated Aug. 20, 2010, for U.S. Appl. No. 10/901,554, filed Jul. 27, 2004, 13 pages.
Non-Final Office Action dated Aug. 22, 2006, for U.S. Appl. No. 10/656,797, filed Sep. 4, 2003, 6 pages.
Non-Final Office Action dated Aug. 25, 2009, for U.S. Appl. No. 10/900,980, filed Jul. 27, 2004, 7 pages.
Non-Final Office Action dated Aug. 26, 2009, for U.S. Appl. No. 11/414,657, filed Apr. 27, 2006, 6 pages.
Non-Final Office Action dated Aug. 29, 2008, for U.S. Appl. No. 10/792,681, filed Mar. 2, 2004, 15 pages.
Non-Final Office Action dated Aug. 30, 2007, for U.S. Appl. No. 11/270,034, filed Nov. 8, 2005, 10 pages.
Non-Final Office Action dated Aug. 9, 2006, for U.S. Appl. No. 10/900,980, filed Jul. 27, 2004, 17 pages.
Non-Final Office Action dated Dec. 22, 2011, for U.S. Appl. No. 11/270,034, filed Nov. 8, 2005, 9 pages.
Non-Final Office Action dated Dec. 27, 2006, for U.S. Appl. No. 10/741,130, filed Dec. 19, 2003, 9 pages.
Non-Final Office Action dated Dec. 27, 2006, for U.S. Appl. No. 11/270,034, filed Nov. 8, 2005, 8 pages.
Non-Final Office Action dated Feb. 10, 2014, for U.S. Appl. No. 12/366,553, filed Feb. 5, 2009, 7 pages.
Non-Final Office Action dated Feb. 17, 2017, for U.S. Appl. No. 14/626,826, filed Feb. 19, 2015, 11 pages.
Non-Final Office Action dated Feb. 18, 2010, for U.S. Appl. No. 11/894,401, filed Aug. 20, 2007, 6 pages.
Non-Final Office Action dated Feb. 2, 2011, for U.S. Appl. No. 12/581,040, filed Oct. 16, 2009, 5 pages.
Non-Final Office Action dated Feb. 27, 2007, for U.S. Appl. No. 11/202,474, filed Aug. 11, 2005, 8 pages.
Non-Final Office Action dated Jan. 13, 2009, for U.S. Appl. No. 10/901,555, filed Jul. 27, 2004, 11 pages.
Non-Final Office Action dated Jan. 19, 2010, for U.S. Appl. No. 11/270,034, filed Nov. 8, 2005, 10 pages.
Non-Final Office Action dated Jan. 23, 2009, for U.S. Appl. No. 11/232,190, filed Sep. 20, 2005, 8 pages.
Non-Final Office Action dated Jan. 23, 2009, for U.S. Appl. No. 11/270,034, filed Nov. 8, 2005, 8 pages.
Non-Final Office Action dated Jan. 26, 2017, for U.S. Appl. No. 13/540,499, filed Jul. 2, 2012, 10 pages.
Non-Final Office Action dated Jan. 29, 2009, for U.S. Appl. No. 10/900,980, filed Jul. 27, 2004, 6 pages.
Non-Final Office Action dated Jan. 31, 2008, for U.S. Appl. No. 11/255,400, on Oct. 20, 2005, 7 pages.
Non-Final Office Action dated Jan. 4, 2007, for U.S. Appl. No. 11/255,400, filed Oct. 20, 2005, 7 pages.
Non-Final Office Action dated Jan. 9, 2008, for U.S. Appl. No. 11/232,190, filed Sep. 20, 2005, 8 pages.
Non-Final Office Action dated Jul. 24, 2007, for U.S. Appl. No. 10/656,797, filed Sep. 4, 2003, 6 pages.
Non-Final Office Action dated Jul. 29, 2011, for U.S. Appl. No. 12/574,563, filed Oct. 6, 2009, 5 pages.
Non-Final Office Action dated Jun. 21, 2010, for U.S. Appl. No. 11/894,397, filed Aug. 20, 2007, 13 pages.
Non-Final Office Action dated Jun. 6, 2008, for U.S. Appl. No. 10/656,797, filed Sep. 4, 2003, 5 pages.
Non-Final Office Action dated Jun. 9, 2010, for U.S. Appl. No. 11/894,468, filed Aug. 20, 2007, 14 pages.
Non-Final Office Action dated Mar. 12, 2007, for U.S. Appl. No. 11/232,190, filed Sep. 20, 2005, 11 pages.

(56) References Cited

OTHER PUBLICATIONS

Non-Final Office Action dated Mar. 16, 2010, for U.S. Appl. No. 11/894,340, filed Aug. 20, 2007, 14 pages.
Non-Final Office Action dated Mar. 18, 2009, for U.S. Appl. No. 10/901,554, filed Jul. 27, 2004, 12 pages.
Non-Final Office Action dated Mar. 27, 2008, for U.S. Appl. No. 10/900,980, filed Jul. 27, 2004, 7 pages.
Non-Final Office Action dated Mar. 27, 2009, for U.S. Appl. No. 10/741,130, filed Dec. 19, 2003, 9 pages.
Non-Final Office Action dated Mar. 29, 2010, for U.S. Appl. No. 11/894,463, filed Aug. 20, 2007, 14 pages.
Non-Final Office Action dated Mar. 31, 2009, for U.S. Appl. No. 10/792,681, filed Mar. 2, 2004, 15 pages.
Non-Final Office Action dated Mar. 5, 2009, for U.S. Appl. No. 11/202,474, filed Aug. 11, 2005, 10 pages.
Non-Final Office Action dated Nov. 14, 2007, for U.S. Appl. No. 10/741,130, filed Dec. 19, 2003, 8 pages.
Non-Final Office Action dated Nov. 14, 2007, for U.S. Appl. No. 11/137,833, filed May 24, 2005, 8 pages.
Non-Final Office Action dated Nov. 15, 2006, for U.S. Appl. No. 11/137,833, filed May 24, 2005, 12 pages.
Non-Final Office Action dated Nov. 24, 2010, for U.S. Appl. No. 10/900,980, filed Jul. 27, 2004, 8 pages.
Non-Final Office Action dated Nov. 24, 2015, for U.S. Appl. No. 14/156,347, filed Jan. 15, 2014, 5 pages.
Non-Final Office Action dated Nov. 28, 2006, for U.S. Appl. No. 10/901,019, filed Jul. 27, 2004, 20 pages.
Non-Final Office Action dated Oct. 13, 2011, for U.S. Appl. No. 12/187,331, filed Aug. 6, 2008, 5 pages.
Non-Final Office Action dated Oct. 19, 2007, for U.S. Appl. No. 11/202,474, filed Aug. 11, 2005, 7 pages.
Non-Final Office Action dated Oct. 19, 2009, for U.S. Appl. No. 10/901,019, filed Jul. 27, 2004, 21 pages.
Non-Final Office Action dated Oct. 19, 2015, for U.S. Appl. No. 14/309,837, filed Jun. 19, 2014, 6 pages.
Non-Final Office Action dated Oct. 24, 2008, for U.S. Appl. No. 10/901,019, filed Jul. 27, 2004, 11 pages.
Non-Final Office Action dated Oct. 25, 2010, for U.S. Appl. No. 11/202,474, filed Aug. 11, 2005, 8 pages.
Non-Final Office Action dated Oct. 29, 2007, for U.S. Appl. No. 10/901,019, filed Jul. 27, 2004, 10 pages.
Non-Final Office Action dated Oct. 29, 2010, for U.S. Appl. No. 11/894,530, filed Aug. 20, 2007, 11 pages.
Non-Final Office Action dated Sep. 17, 2009, for U.S. Appl. No. 10/656,797, filed Sep. 4, 2003, 13 pages.
Non-Final Office Action dated Sep. 26, 2008, for U.S. Appl. No. 11/414,657, filed Apr. 27, 2006, 11 pages.
Notice of Allowance dated Apr. 28, 2010, for U.S. Appl. No. 10/901,019, filed Jul. 27, 2004, 7 pages.
Notice of Allowance dated Aug. 16, 2018, for U.S. Appl. No. 15/265,781, filed Sep. 14, 2016, 7 pages.
Notice of Allowance dated Aug. 4, 2009, for U.S. Appl. No. 10/901,555, filed Jul. 27, 2004, 7 pages.
Notice of Allowance dated Dec. 19, 2017, for U.S. Appl. No. 14/626,826, filed Feb. 19, 2015, 8 pages.
Notice of Allowance dated Dec. 6, 2010, for U.S. Appl. No. 12/132,375, filed Jun. 3, 2008, 9 pages.
Notice of Allowance dated Feb. 24, 2010, for U.S. Appl. No. 10/656,797, filed Sep. 4, 2003, 8 pages.
Notice of Allowance dated Jul. 26, 2011, for U.S. Appl. No. 11/894,530, filed Aug. 20, 2007, 10 pages.
Notice of Allowance dated Jun. 11, 2012, for U.S. Appl. No. 10/741,130, filed Dec. 19, 2003, 9 pages.
Notice of Allowance dated Jun. 15, 2016, for U.S. Appl. No. 14/156,347, filed Jan. 15, 2014, 7 pages.
Notice of Allowance dated Jun. 22, 2018, for U.S. Appl. No. 15/265,781, filed Sep. 14, 2016, 8 pages.
Notice of Allowance dated Mar. 17, 2014, for U.S. Appl. No. 12/366,553, filed Feb. 5, 2009, 8 pages.
Notice of Allowance dated Mar. 2, 2015, for U.S. Appl. No. 12/187,331, filed Aug. 6, 2008, 5 pages.
Notice of Allowance dated Nov. 17, 2010, for U.S. Appl. No. 11/232,190, filed Sep. 20, 2005, 11 pages.
Notice of Allowance dated Nov. 8, 2017, for U.S. Appl. No. 13/820,447, filed Oct. 18, 2013, 8 pages.
Notice of Allowance dated Oct. 29, 2015, for U.S. Appl. No. 10/901,554, filed Jul. 27, 2004, 8 pages.
Notice of Allowance dated Sep. 25, 2013, for U.S. Appl. No. 12/132,161, filed Jun. 3, 2008, 12 pages.
Shumway, S.J. et al. (Dec. 1988). "A 'Designer' Annuloplasty Ring for Patients with Massive Mitral Annular Dilatation," *Ann. Thorac. Surg.* 46(6):695-696.
Supplementary European Search Report dated Nov. 10, 2008, for EP Application No. 04 78 2847, filed on Sep. 1, 2004, 2 pages.
U.S. Appl. No. 11/875,774, filed Oct. 19, 2007, by Serina et al.
Written Opinion dated Nov. 17, 2016 in PCT Application No. PCT/US2016/032220 filed May 12, 2016. 4 pages.
Written Opinion of the International Searching Authority dated Apr. 2, 2007, for PCT Application No. PCT/US2006/043597, filed Nov. 8, 2006, 7 pages.
Written Opinion of the International Searching Authority dated Dec. 19, 2006, for PCT Application No. PCT/US2006/031190, filed Aug. 10, 2006, 6 pages.
Written Opinion of the International Searching Authority dated Mar. 7, 2007, for PCT Patent Application No. PCT/US2004/028431, filed on Sep. 1, 2004, 4 pages.
Written Opinion of the International Searching Authority dated Sep. 19, 2009, for PCT Patent Application No. PCT/US2009/033252, filed on Feb. 5, 2009, 8 pages.
Extended European Search Report dated Jan. 21, 2019, for EP Patent Application No. 16793570.9, filed on May 12, 2016, 9 pages.
Extended European Search Report dated Dec. 12, 2018, for EP Patent Application No. 18170269.7, filed on Sep. 1, 2004, 7 pages.
Non-Final Office Action dated Mar. 28, 2019, for U.S. Appl. No. 15/652,068, filed Jul. 17, 2017, 11 pages.
Notice of Allowance dated Sep. 16, 2019, for U.S. Appl. No. 15/652,068, filed Jul. 17, 2017, 8 pages.
U.S. Appl. No. 16/749,647, filed Jan. 22, 2020, by Nguyen et al.
Notice of Allowance dated Feb. 24, 2020, for U.S. Appl. No. 15/955,564, filed Apr. 17, 2018, 9 pages.

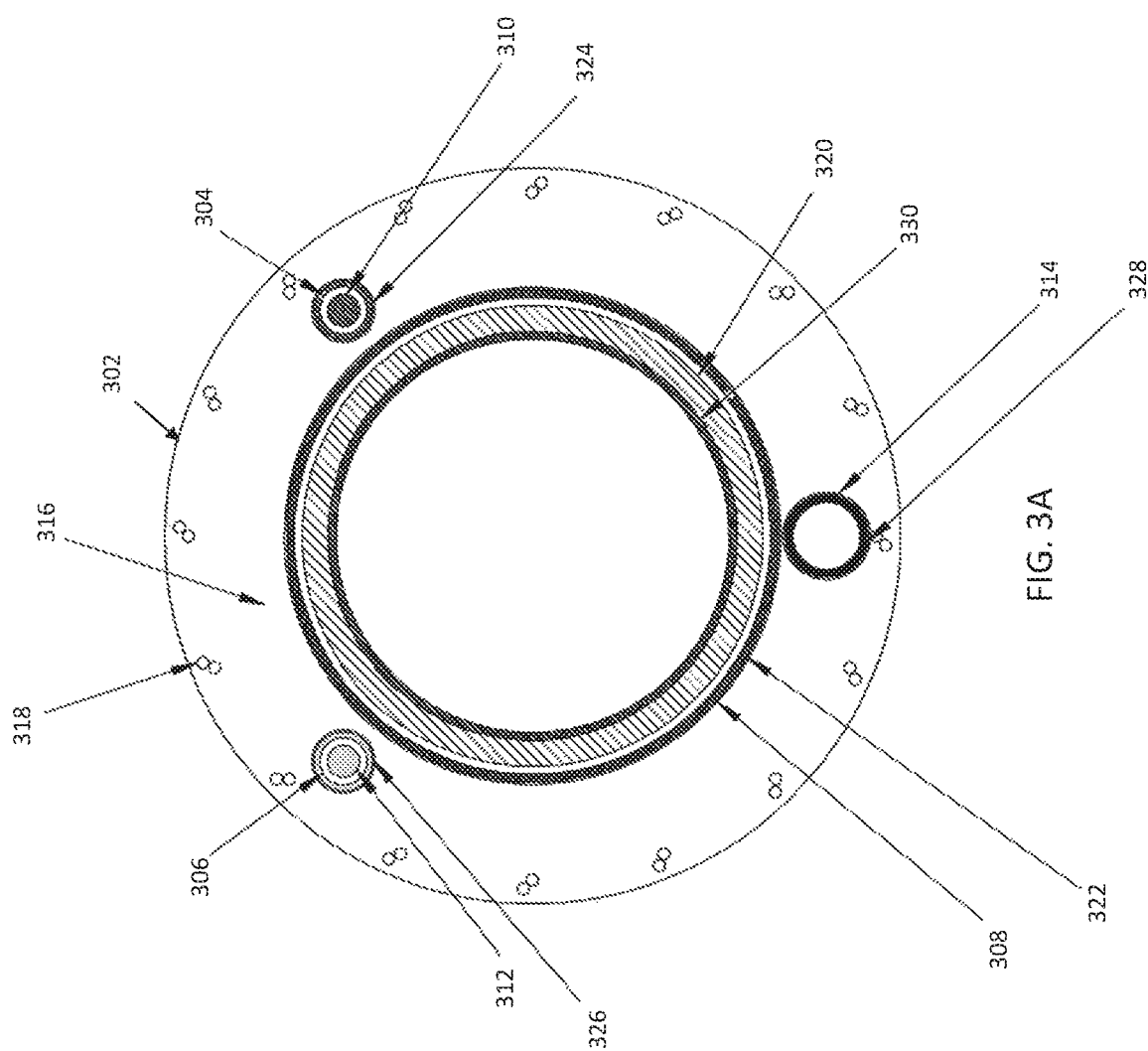

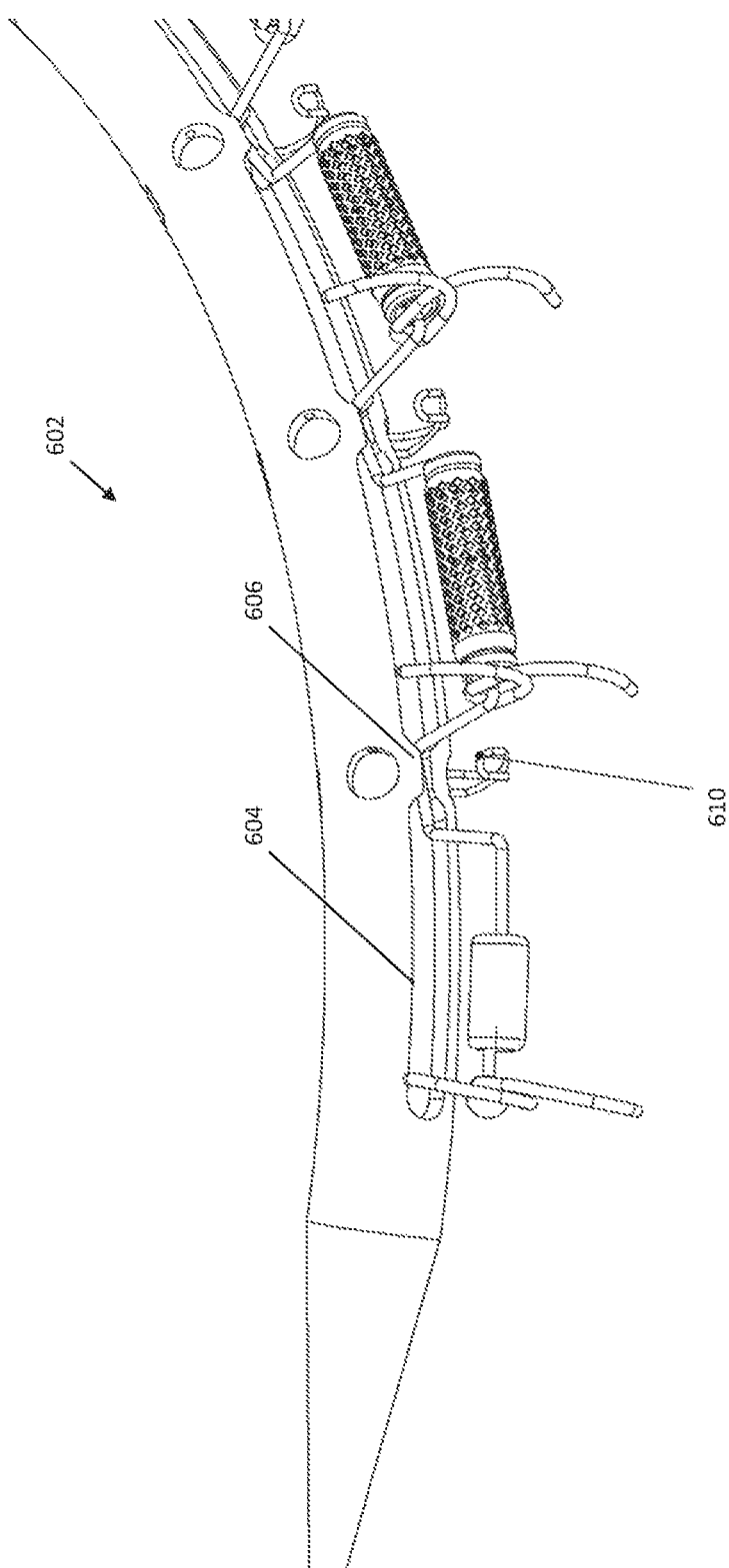

DEVICE AND METHOD FOR RELEASING CATHETERS FROM CARDIAC STRUCTURES

CROSS-REFERENCE TO RELATED APPLICATIONS

This application is a U.S. National Phase Application under 35 U.S.C. § 371 of International Application No. PCT/US2016/032220, filed on May 12, 2016, which designated the United States, which claims priority to U.S. Provisional Application Ser. No. 62/160,595, filed on May 12, 2015, each of which is hereby incorporated by reference in its entirety.

FIELD

The present invention is directed toward devices, systems, and methods for performing a heart procedure.

BACKGROUND

Blood returning to the heart from peripheral circulation and the lungs generally flows into the atrial chambers of the heart and then to the ventricular chambers, which pump the blood back out of the heart. During ventricular contraction, the atrio-ventricular valves between the atria and ventricles (i.e. the tricuspid and mitral valves), close to prevent backflow or regurgitation of blood from the ventricles back to the atria. The closure of these valves, along with the aortic and pulmonary valves, maintains the unidirectional flow of blood through the cardiovascular system. Disease of the valves can result in valve dysfunction, where some fraction of the ventricular blood regurgitates back into the atrial chambers.

Treatment of heart valve stenosis or regurgitation, such as mitral or tricuspid regurgitation, may involve an open-heart surgical procedure to replace or repair the valve. Methods and devices have been developed to accomplish ventriculoplasty on the left ventricle of the human heart for patients suffering from functional mitral valve regurgitation and/or congestive heart failure. A device such as a delivery catheter may be advanced into the heart to place a set of anchors within the left ventricular myocardium in a subannular region between the mitral annulus and the papillary muscles. The anchors are coupled together by a tether. Once the anchors and tether are released, the tether is cinched in order to reduce the mitral annulus, creating mitral valve competence and relieving left ventricle wall stress. Additional devices and methods for releasing anchor structures from a catheter may be desirable.

BRIEF SUMMARY

Described here are devices, systems, and methods for removing a catheter from a body organ. In general, the systems described here for delivering an implant comprise a catheter comprising a longitudinal axis, a first elongate element lumen, a second elongate element lumen, a tissue anchor lumen, and a plurality of apertures along the longitudinal axis. The plurality of apertures may comprise first elongate element apertures, second elongate element apertures, and tissue anchor apertures. The catheter may further comprise a plurality of retaining portions each between adjacent tissue anchor apertures and between adjacent first and second elongate element apertures. A first elongate element may be disposed within the first elongate element lumen. A second elongate element may be disposed within the second elongate element lumen. For each pair of adjacent first and second elongate element apertures, the first elongate element may extend out of the first elongate element lumen through the first elongate element aperture across the retaining portion transversely with respect to the longitudinal axis and towards the second elongate element aperture. The first elongate element may extend into the second elongate element aperture, loop over the second elongate element, and extend back across the retaining portion and into the first elongate element lumen.

In some variations, the first elongate element may be releasably coupled to the second elongate element. In other variations, the first elongate element extending between the first and second elongate element apertures may cross over itself. In yet other variations, the first elongate element may be fixed to a distal end of the catheter.

In some variations, a first elongate element control may be configured to retract the first elongate element from the first elongate element lumen and a second elongate element control may be configured to retract the second elongate element from the second elongate element lumen. In some of these variations, retracting the first elongate element from the first elongate element lumen may tension the first elongate element.

In some variations, the plurality of retaining portions may each comprise a channel along the longitudinal axis. In some of these variations, the plurality of retaining portions may be each adapted to open the channel.

In yet further variations, at least one radiopaque structure may be located between the plurality of apertures.

In some variations, an anchor delivery catheter may be advanceable within the catheter and a plurality of tissue anchors within the anchor delivery catheter. In some of these variations, the tissue anchor apertures may be configured for passage of the plurality of tissue anchors. In another of these variations, the anchor delivery catheter may be advanceable within the tissue anchor lumen.

Also described here are methods for performing a procedure inside a heart. In general, the methods comprise positioning a catheter adjacent to heart tissue. The catheter may comprise a longitudinal axis, a first elongate element lumen, a second elongate element lumen, a tissue anchor lumen, and a plurality of apertures along the longitudinal axis. The plurality of apertures may comprise first elongate element apertures, second elongate element apertures, and tissue anchor apertures. The catheter may further comprise a plurality of retaining portions each between adjacent tissue anchor apertures and between adjacent first and second elongate element apertures. A first elongate element may be disposed within the first elongate element lumen and a second elongate element may be disposed within the second elongate element lumen. The plurality of retaining portions may each comprise a channel along the longitudinal axis. For each pair of adjacent first and second elongate element apertures, the first elongate element may extend out of the first elongate element lumen through the first elongate element aperture across the retaining portion transversely with respect to the longitudinal axis and towards the second elongate element aperture. The first elongate element may extend into the second elongate element aperture, loop over the second elongate element, and extend back across the retaining portion and into the first elongate element lumen. A first tissue anchor and at least a second tissue anchor may be deployed into the heart tissue. A tether may couple the first tissue anchor to at least the second tissue anchor. The second elongate element may be retracted from the second elongate element lumen to uncouple the first elongate element from the second elongate element and to open the channel for passage of the first and second tissue anchors. The uncoupled first elongate element may be tensioned. The catheter may be removed from the heart.

In some variations, the catheter may be temporarily secured to heart tissue using at least one of the first and second tissue anchor. In other variations, retracting the second elongate element may increase slack of the first elongate element. In yet other variations, retracting the second elongate element may open the channel. In some variations, the first elongate element may cross over itself. In other variations, the first elongate element may be tensioned against the second elongate element. In yet other variations, the catheter may be indirectly visualized. In some variations, an anchor delivery catheter may be advanced within the catheter.

BRIEF DESCRIPTION OF THE DRAWINGS

FIGS. 3A-3B are proximal and distal cross-sectional views of an illustrative variation of a catheter.

FIGS. 6A and 6C-6E are perspective views of an illustrative variation of tissue anchors and a distal end of a catheter.

DETAILED DESCRIPTION

Described here are devices, systems, and methods for detaching or decoupling an outer catheter from an implanted device during a heart procedure, such as from a subannular region of the left ventricle. Generally, the devices and systems described here are used to reshape atrio-ventricular valves or myocardium to improve hemodynamic performance. The implantation procedures are preferably transvascular, minimally invasive surgical procedures, but can also be performed with open or limited access surgical procedures.

Figure 1:
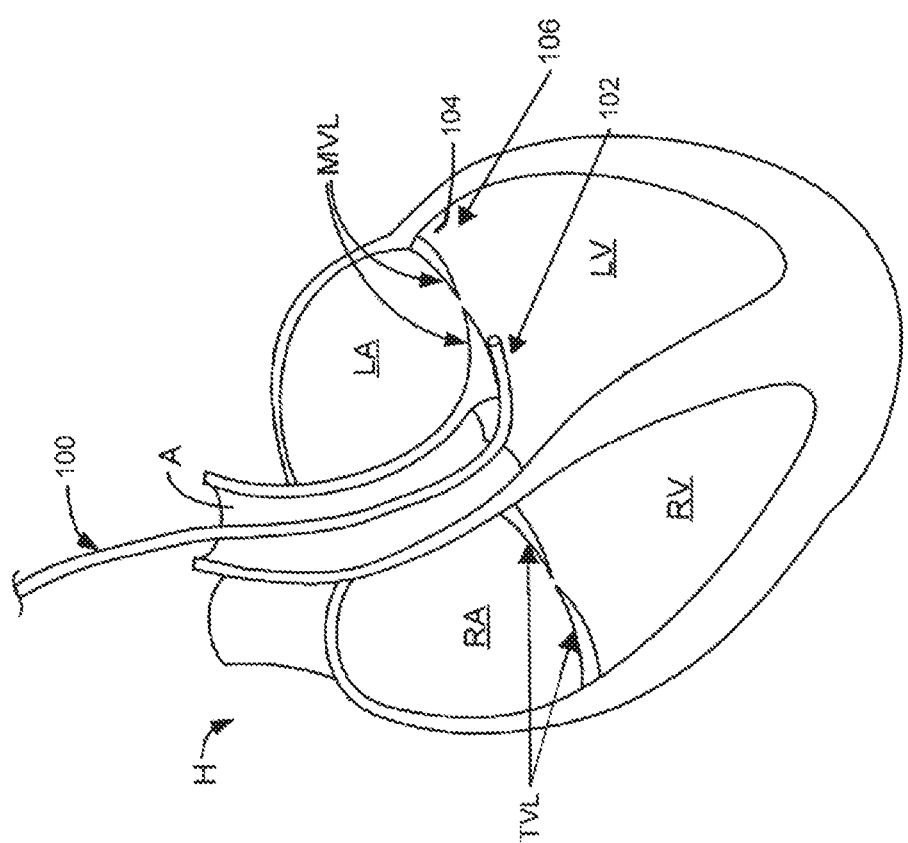
FIG. 1 is a cross-sectional view of a heart with a catheter advanced through the aorta and into the left ventricle.

In instances where the heart is the relevant anatomy, it may be helpful to briefly identify and describe the relevant heart anatomy. FIG. 1 is a cross-sectional depiction of a heart H having a right atrium RA, right ventricle RV, left atrium LA, and left ventricle LV. Tricuspid valve leaflets TVL are provided between the right atrium RA and the right ventricle RV, and mitral valve leaflets MVL are provided between the left atrium LA and left ventricle LV. A catheter 100 is shown being advanced in a retrograde direction through the aorta A and into the left ventricle LV. This access route is used to reach the subvalvular space 106. Retrograde, as used herein, generally refers to a direction opposite the expected flow of blood.

Catheter 100 is generally a flexible elongate catheter which may have one or more curves or bends towards its distal end to facilitate placement of the distal end 102 of the catheter 100 at a desired location. The subvalvular space, as used herein, generally includes the portion of the ventricular chamber that is bound peripherally by the ventricular wall, superiorly by the atrio-ventricular valve leaflets, and centrally by the primary chordae tendineae, and is located along the circumference of the valve annulus. The subannular groove region 104, as used herein, includes the space bordered by the inner surface of the ventricular wall, the inferior surface of valve leaflets MVL, and the third order chordae tendineae connected directly to the ventricular wall and the leaflet MVL.

The distal end 102 of catheter 100 may be configured to be positioned at an opening into the subvalvular space 106 or within the subvalvular space 106, such that subsequent devices may be passed through catheter 100 into the subvalvular space 106. Although the retrograde aortic access route may begin from a percutaneous or peripheral access site, aortic access may alternatively be achieved by an incision in the ascending aorta, descending aorta, aortic arch or iliac arteries, following surgical, thorascopic or laparoscopic access to a body cavity.

I. Devices and Systems

Described here are devices and systems for detaching or decoupling an outer catheter from an implant. For example, a decoupled outer catheter may be removed from a subannular region of the left ventricle of the heart after deployment of the implant from the outer catheter into heart tissue. For example, the outer catheters described here may be used in beating heart procedures where it may be difficult to control the position of the distal end of an anchor delivery catheter with respect to the target tissue. Generally, an outer catheter comprises a plurality of lumens and apertures along a longitudinal axis of the outer catheter. The implant may comprise one or more tissue anchors that may be advanced through a tissue anchor lumen of the outer catheter. The tissue anchors may be coupled together by a tether. A plurality of tissue anchor apertures may be arranged longitudinally at a distal portion of the outer catheter to allow the tissue anchors to be delivered out of corresponding tissue anchor apertures.

In one variation, an implant delivery system may comprise an outer catheter and an inner catheter slidable within the outer catheter. An anchor delivery catheter may be slidable within the inner catheter. Once the outer catheter has been positioned at its desired location, it need not be moved relative to heart tissue to deploy an implant (e.g., a plurality of tissue anchors). Instead, the anchor delivery catheter and/or inner catheter may be manipulated within the non-moving outer catheter to deploy the tissue anchors through a desired tissue anchor aperture. The outer catheter also permits delivery of tissue anchors with predetermined spacing and/or alignment with respect to each other. Thus, the outer catheter may reduce the risk that during a lengthy procedure with multiple anchoring sites, repositioning of the anchor delivery catheter to a new target location may dislodge the anchor delivery catheter and/or the implant from heart tissue.

After deployment of tissue anchors from the outer catheter, portions of the implant (e.g., tether) may be retained within the outer catheter until a mechanism is actuated that allows the tether to be released from the outer catheter. The devices and system discussed below comprise an implant release mechanism that allows the tissue anchors to completely separate and release from the outer catheter with minimal force and physical interference, thereby reducing the risk of damage to the system and tissue. For instance, the implant release mechanism may be operated in a manner where the mechanism does not interfere with any of a tissue anchor, tether, outer catheter, and heart tissue. The implant release mechanism may be easily operated from a hub and may utilize, but need not require, direct or indirect visualization.

Figure 2A:
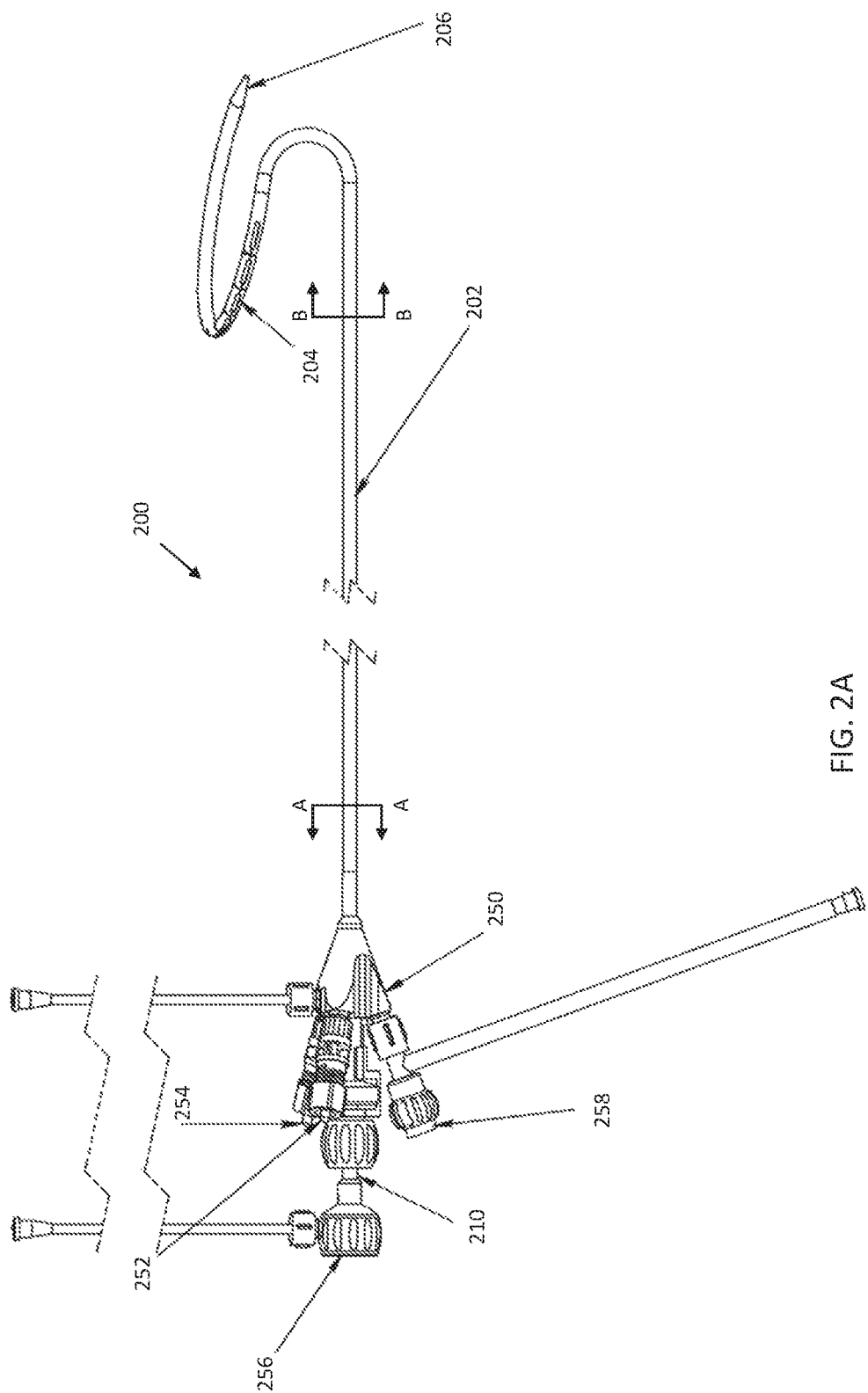
FIGS. 2A-2C are side and perspective views of an illustrative variation of a catheter and proximal hub.

One variation is illustrated in the side view of FIG. 2A. As depicted, an implant delivery system may comprise an outer catheter 202 and hub 250. A distal end of the outer catheter 202 may comprise tissue anchor apertures 204 and an atraumatic distal tip 206. The tissue anchor apertures 204 may be sized for passage of tissue anchors (not shown) delivered through the outer catheter 202. An inner catheter 210 may be disposed through at least a portion of the outer catheter 202. As described in more detail below, an outer catheter may comprise a plurality of lumens to engage with one or more other outer catheters and release one or more implants from the catheter, such as heart tissue anchors.

A hub 250 is coupled to a proximal end of the outer catheter 202. As depicted in FIGS. 2A and 2C, the hub 250 may comprise a plurality of ports including a first elongate element control port 252, a second elongate element control port 254, inner catheter port 256, and guidewire port 258. The hub may further comprise flush ports for outer catheter 202 and inner catheter 210. The first and second elongate element control ports 252, 254 may be controlled by a user to unlock the outer catheter 202 to release tissue anchors from the outer catheter 202, as described in more detail below.

Outer Catheter

Figure 2B:
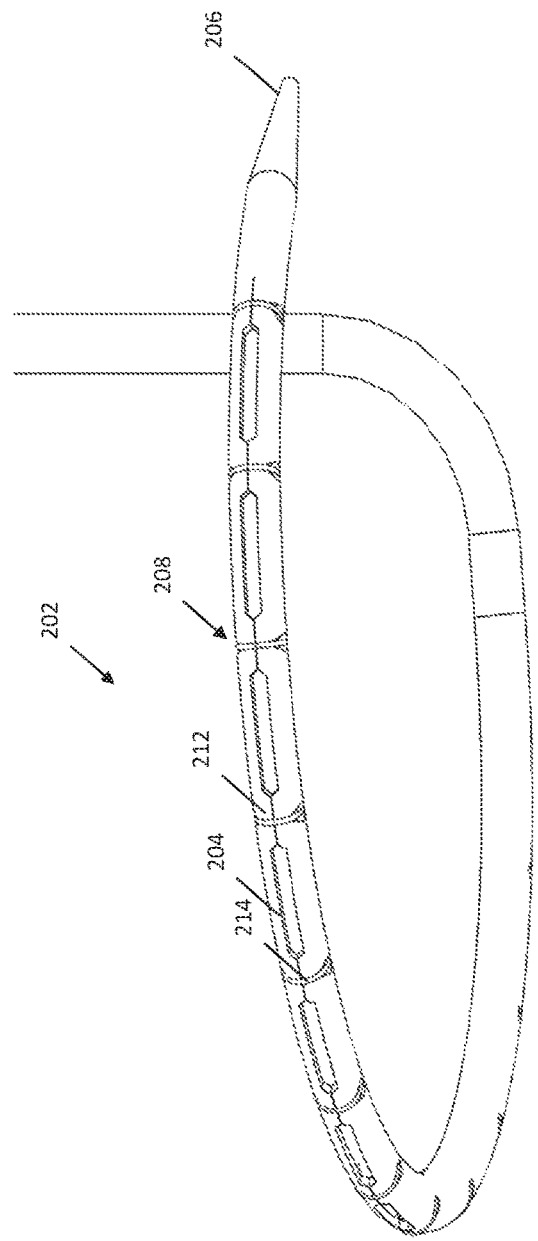
Figure 2C:
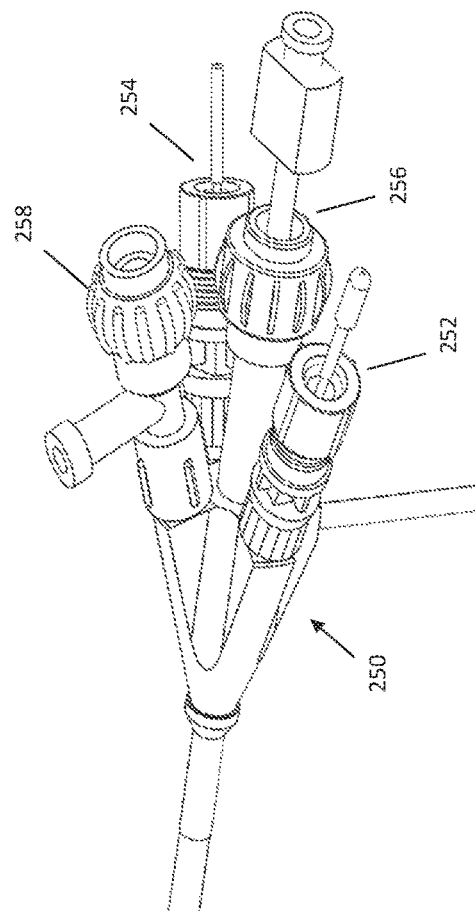

A perspective view of the distal portion of outer catheter 202 is illustrated in FIG. 2B and comprises a distal tip 206 and a plurality of tissue anchor apertures 204. In some variations, the outer catheter may comprise 11 or 13 apertures. In some of these variations, two tissue anchors may be deployed out of the proximal-most aperture such that a total of 12 or 14 anchors may be deployed from a respective outer catheter. An outer catheter may comprise any number of apertures, for example, 4, 6, 7, 10, 12, 15, 16, 17, 20, 24 or more apertures. The distal portion of the outer catheter 202 as shown in FIG. 2B may comprise a curvature configured to facilitate the placement of tissue anchors in a subannular groove region. In this manner, the distal portion may more easily conform to the geometry of the atrio-ventricular valve. As discussed in further detail below, fluoroscopic visualization of radiopaque structures of the outer catheter may help position and/or align the outer catheter to a desired tissue region.

An implant release mechanism 208 may be provided between adjacent apertures 204 and include a retaining portion 212 that separates adjacent tissue anchor apertures 204. A first elongate element 214 may extend transversely relative to a longitudinal axis of the outer catheter 202 across an external surface of the outer catheter 202 to hold the retaining portion 212 in a closed configuration that promotes stability of the outer catheter 202 during delivery of an implant (e.g., tissue anchors). As will be discussed in more detail with respect to FIGS. 4A-4C and 6A-6E, an implant release mechanism is actuated such that a longitudinal channel within the retaining portion may open to allow the passage of a tether coupled to tissue anchors to be completely released from the outer catheter.

Lumens

Figure 3B:
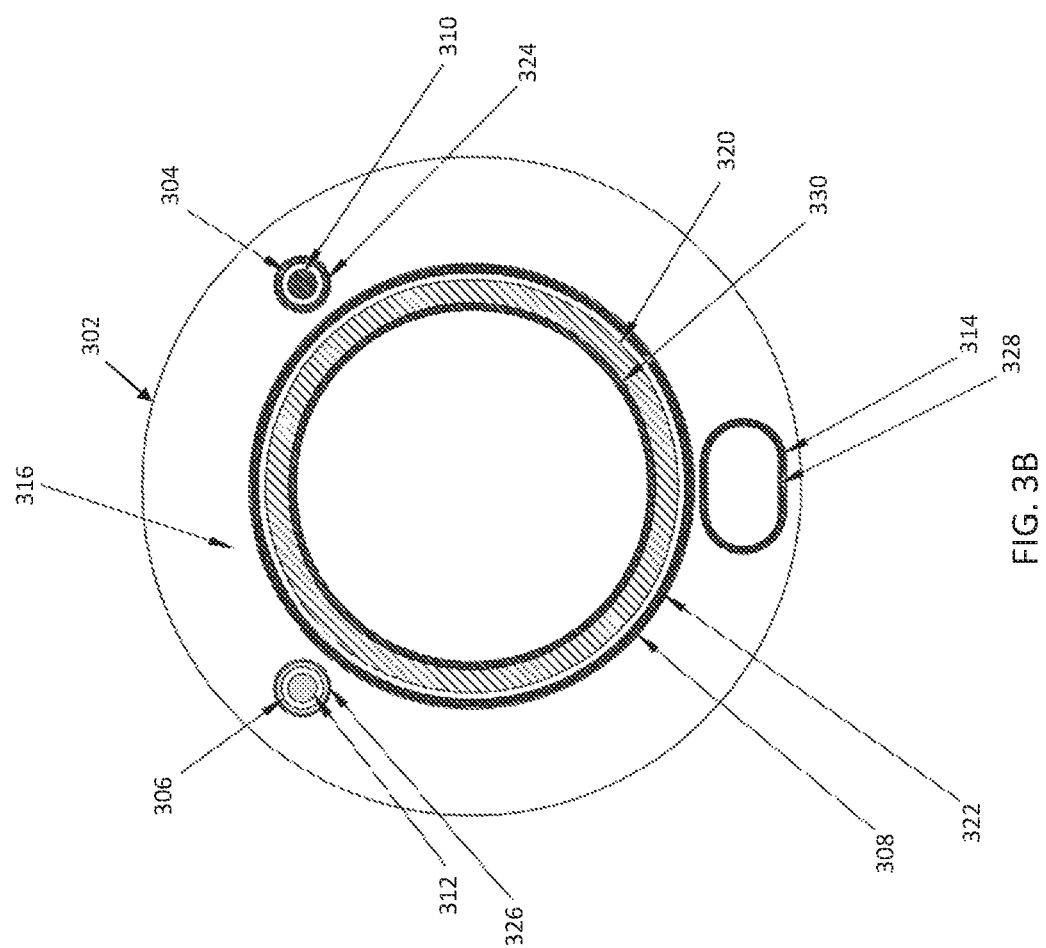

FIG. 3A depicts a cross-sectional view of a proximal end of an illustrative variation of an outer catheter 302 as viewed from the A-A line of FIG. 2A. FIG. 3B depicts a cross-sectional view of a distal end of outer catheter 302 as viewed from the B-B line of FIG. 2A. The outer catheter 302 may include a first elongate element lumen 304 having a first elongate element 310 disposed therein and a second elongate element lumen 306 having a second elongate element 312 disposed therein. In some variations, the second elongate element lumen 306 may extend from a distal portion of an outer catheter 302 to a hub. A diameter of the second elongate element 312 may range from about 0.10 mm to about 0.30 mm and may be, for example, a 0.203 mm diameter. The first elongate element lumen 304 may extend from a distal portion of the outer catheter 302 to a hub. A diameter of the first elongate element 312 may range from about 0.10 mm to about 0.30 mm and may be, for example, a 0.254 mm diameter first elongate element 310.

A guidewire lumen 314 may be provided for a guidewire (not shown) to provide relative movement between the outer catheter 302 and guidewire. For example, the guidewire may first be advanced from the descending aorta, through the left ventricle into subvavular space behind chordae tendineae, and positioned in a subannular groove region. Then, the outer catheter 302 may be advanced over the guidewire to position the outer catheter 302 in the subannular groove region under the mitral valve. Accordingly, the guidewire may be used as a rail for outer catheter placement. Once the outer catheter 302 is advanced to a desired position, the guidewire may remain in place throughout a procedure to facilitate ease of use and safety. For example, the guidewire may function as a rail and a position locator if there is a need to remove and replace the outer catheter during the procedure. Additionally or alternatively, the guidewire may extend out of the distal end of the outer catheter and form an atraumatic tip. Alternatively, once the outer catheter 302 is advanced to a desired position, the guidewire may be withdrawn proximally from the guidewire lumen 314, and out of a guidewire port.

The guidewire lumen 314 may form a circular cross-section at a proximal end of the outer catheter 302 (FIG. 3A) and an oval cross-section at a distal end of the outer catheter 302 (FIG. 3B). In some variations, the guidewire may have a diameter in a range of about 0.20 mm to about 0.60 mm and may be, for example, 0.457 mm in diameter. The proximal and distal lumens in FIGS. 3A-3B coincide and may run the entire length of the outer catheter 302 shaft. While the cross-sectional shape of the guidewire lumen may vary across the length of the outer catheter, it should be understood that in other variations, the cross-sectional shape of the guidewire lumen may be the same across the length of the outer catheter. The cross-section of a guidewire lumen may be similar to that of a circle, oval, ellipse, square, rectangle, etc.

In some variations, one or more of the lumens may comprise a liner to reinforce the lumen or provide a friction different than that of the lumen. For example, a lumen may comprise a material such as PEBAX, and a liner may have a high friction coefficient and/or may comprise a material such as PTFE. For instance, FIGS. 3A and 3B depict a tissue anchor lumen liner 322, a first elongate element lumen liner 324, a second elongate element lumen liner 326, a guidewire lumen liner 328, and an inner catheter lumen liner 330. A tissue anchor lumen liner 322 may be provided on a surface of the tissue anchor lumen 308 and may be between the outer catheter 302 and inner catheter 330. The inner catheter 320 may be provided between the tissue anchor lumen liner 322 and the inner catheter lumen liner 330. The inner catheter lumen liner 330 may be provided on an internal surface of the inner catheter 320. First elongate element lumen liner 324 may be provided on a surface of the first elongate element lumen 304. Second elongate element lumen liner 326 may be provided on a surface of the second elongate element lumen 306. Guidewire lumen liner 328 may be provided on a surface of the guidewire lumen 314.

In some variations, the outer catheter 302 may comprise a polymer jacket 316 and/or braid reinforcement 318 to reinforce the outer catheter 302 and/or alter the flexibility of the outer catheter 302. A polymer jacket may be made, for example, from a low stiffness material in order to form a flexible catheter, while the braid reinforcement may be braided with a pitch to improve torque transmission without significantly increasing stiffness. Braid reinforcement 318 may be provided within the polymer jacket 316 in a spaced apart manner away from a lumen side of the outer catheter 302. In some variations, a distal end of the outer catheter 302 may decrease in diameter relative to the proximal end, and may be provided without braid reinforcement. Accordingly, the distal end of the outer catheter 302 may be more flexible than a proximal end of the outer catheter 302.

Inner Catheter

In some variations, an implant delivery system may comprise an inner catheter 320 slidable within a tissue anchor lumen 308 of the outer catheter 302, as shown in FIGS. 3A-3B. The inner catheter 320 may have an inner catheter lumen through which an anchor delivery catheter (not shown) having a plurality of tissue anchors that may be advanced through the tissue anchor lumen 308. In some variations, inner catheter 320 may be used to simplify positioning of one or more anchor delivery catheters with respect to deployment of tissue anchors from the outer catheter 302. For instance, inner catheter 320 may comprise a single aperture at a distal end of the inner catheter 320. This aperture may be sequentially aligned with each tissue anchor aperture of the outer catheter 302 in order to sequentially deliver anchors at each tissue site corresponding to the location of each tissue anchor aperture. That is, aligning the aperture of the inner catheter with a desired tissue anchor aperture of the outer catheter may help to facilitate the positioning of an anchor delivery catheter by ensuring that when the anchor delivery catheter is advanced into and reaches the distal end of the inner catheter, the delivery aperture(s) of the anchor delivery catheter is aligned with the desired tissue anchor aperture. A tissue anchor deployed from the anchor delivery catheter exits out of the aperture of the inner catheter 320 through an aligned tissue anchor aperture of the outer catheter 302. The inner catheter 320 may thus facilitate tissue anchor deployment through the tissue anchor apertures of outer catheter 302. Alternatively, the anchor delivery catheter itself may exit aligned apertures of the inner and outer catheters (FIGS. 7D-7E), and may, in some instances, contact the tissue into which the anchor is to be deployed. A user is assured that alignment of the inner catheter 320 relative to the outer catheter 302 also aligns an anchor delivery catheter with the outer catheter 302.

Implant Release Mechanism

An implant release mechanism as depicted in FIGS. 4A-4C and FIGS. 5A-5B may provide releasable retention of tethered tissue anchors without requiring repositioning of the outer catheter for each anchor. At least a portion of a tether may be held within a lumen of the outer catheter until actuation of the implant release mechanism. In some variations, components of the implant release mechanism may be withdrawn (e.g., elongate elements) into the outer catheter to prevent interference of the implant release mechanism with the implant and/or heart tissue. As referred to herein, an implant may comprise a plurality of tissue anchors slidably coupled by a tether.

Figure 4A:
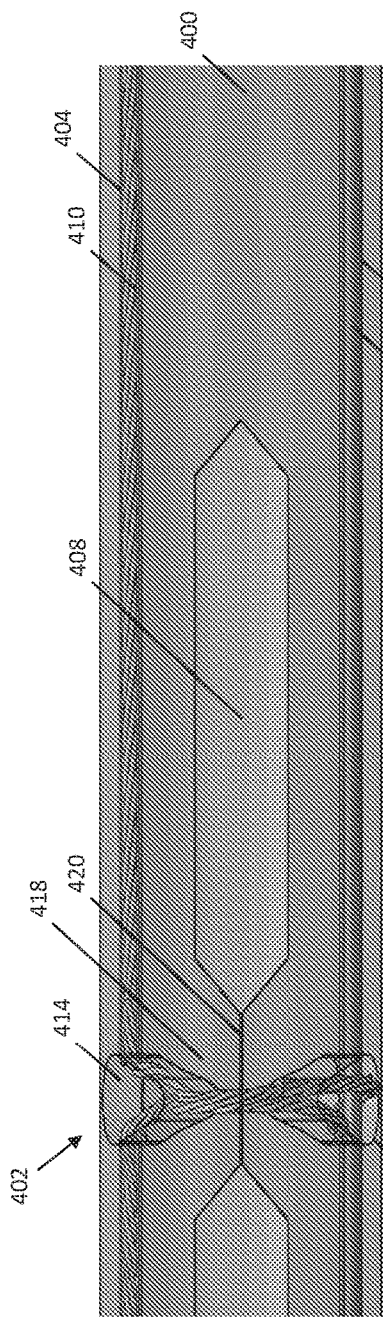
FIGS. 4A-4C are detailed side views of an illustrative variation of an implant release mechanism of a catheter.
Figure 4B:
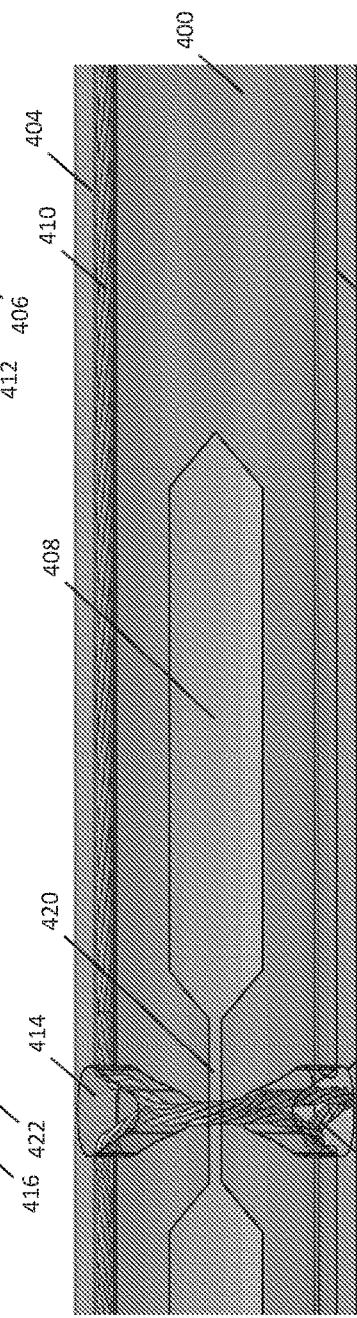
Figure 4C:
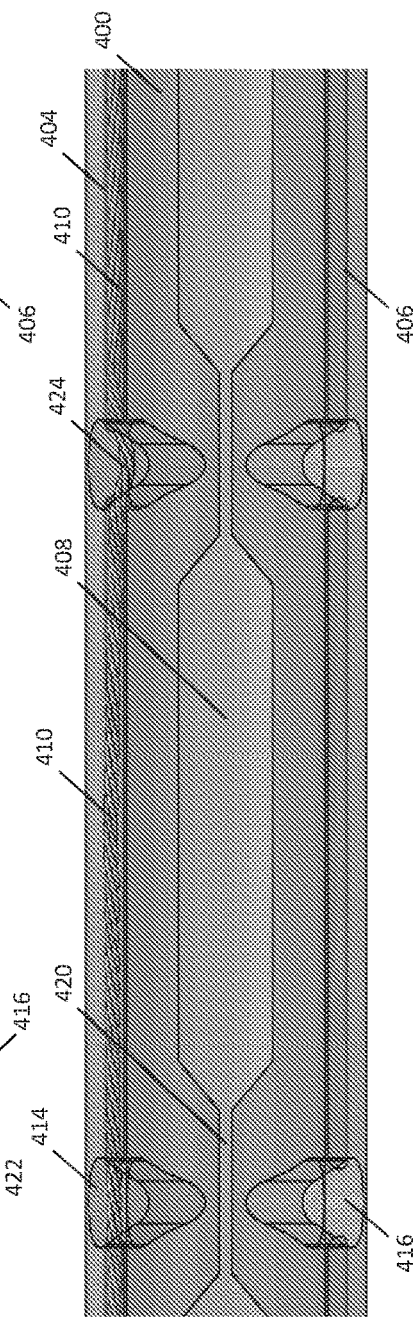

FIG. 4A provides a detailed side view of outer catheter 400 including implant release mechanism 402 having a first elongate element lumen 404 and a second elongate element lumen 406. In FIGS. 4A-4C, outer catheter 400 is depicted as partially transparent in order to better show the elongate elements and lumens. A first elongate element 410 is disposed within the first elongate element lumen 404 and a second elongate element 412 is disposed within the second elongate element lumen 406.

The outer catheter 400 may further comprise a plurality of tissue anchor apertures 408 along a longitudinal axis of the outer catheter 400. The tissue anchor apertures 408 may open into a tissue anchor lumen of the outer catheter 400. The first and second elongate element lumens 404, 406 are provided parallel to the longitudinal axis of the outer catheter 404 on either side of the tissue anchor apertures 408.

The outer catheter 400 may include one or more first elongate element apertures 414 and second elongate element apertures 416. The first and second elongate element apertures 414, 416 open into respective first and second elongate element lumens 404, 406. The first and second elongate element apertures 414, 416 may be any size and shape that allows the first elongate element 410 to exit and enter the first and second elongate element apertures 414, 416. Adjacent first and second elongate element apertures 414, 416 in the transverse direction with respect to the longitudinal axis are referred to as an elongate element aperture pair.

A retaining portion 418 may be provided between adjacent tissue anchor apertures 408 and an elongate element aperture pair. The retaining portion 418 may comprise a polymer wall structure that separates adjacent tissue anchor apertures 408 and first and second elongate element apertures 414, 416. The retaining portion 418 may comprise a channel 420 that is adapted to be in a locked, closed configuration (FIGS. 4A, 5A-5B) and an unlocked, open configuration (FIGS. 4B-4C). In some variations, a channel width may be from about 0.5 mm to about 0.8 mm in the open configuration. In some variations, a channel width may be 0.0 mm to about 0.4 mm in the closed configuration. Each of the channels 420 may extend along the longitudinal axis of the outer catheter 400. Edges of the channel 420 move away from each other in the open configuration to form an aperture between the edges.

As shown in FIGS. 4A-4B, the first elongate element 410 may be releasably coupled to the second elongate element 412. For each pair adjacent first and second elongate element apertures 414, 416, the first elongate element 410 may extend out of the first elongate element lumen 404 through the first elongate element aperture 414, and extend across the retaining portion 418 in a transverse direction with respect to the longitudinal axis of the outer catheter 400. The first elongate element 410 may cross over an external surface of the outer catheter 400 and over the closed channel 420 towards the second elongate element aperture 416. The external surface is, for example, an exterior of the outer catheter 400.

The first elongate element 410 may extend into the second elongate element aperture 416 and loop 422 over the second elongate element 412 to couple the first and second elongate elements 410, 412 to each other. The first elongate element 410 may extend out of the second elongate element aperture 416 and extend back across over the external surface of the outer catheter 400, the channel 420, and retaining portion 418. The first elongate element 410 may extend into the first elongate element aperture 414 and back into the first elongate element lumen 404.

A locked configuration of the implant release mechanism refers herein to the configuration shown in FIG. 4A where first elongate element 410 is looped over the second elongate element 412. If the channel 420 is open in the locked configuration, a tether of the implant will be retained by the first elongate element 410 to maintain the connection between the outer catheter 400 and the implant. However, when the first elongate element 410 is looped and tensioned against the second elongate element 416, the channel 420 is provided in the closed configuration.

Figure 5A:
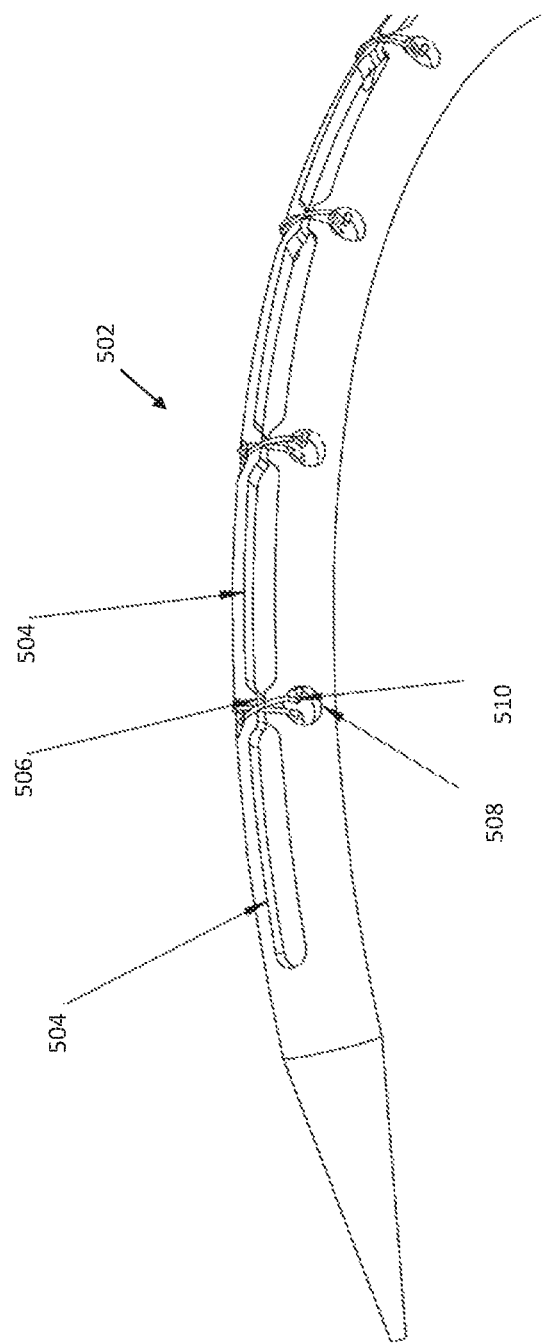
FIGS. 5A-5B are perspective views of an illustrative variation of a distal end of a catheter.
Figure 5B:
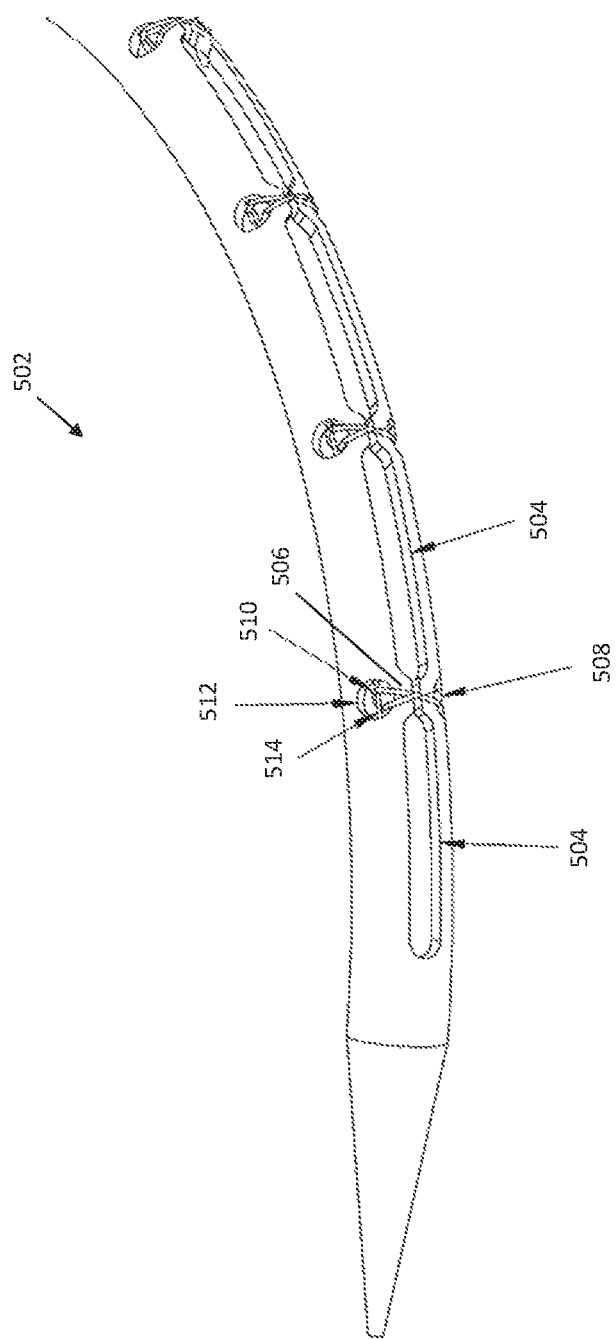

In some variations, the first elongate element 410 extending between the first and second elongate element apertures 414, 416 (over the retaining portion 418) crosses over or intertwines itself, as shown in FIGS. 5A-5B.

In some variations, the first elongate element 410 may be formed of any material that may be looped and tensioned around the second elongate element 412. In some instances, the first elongate element 410 may be a fiber cable such as a flexible, twistable, and/or lubricious cable. In some variations, the first elongate element 410 may be fixed to a distal end of the outer catheter 400 (not shown). In some instances, a distal end of the first elongate element 410 may be terminated in the first elongate element lumen 404 by a knot or any other suitable method such that the first elongate element 410 is fixed and remains secured to the outer catheter 400 when a proximal end of the first elongate element 410 is retracted from the first elongate element lumen 404. This allows the tension of the first elongate element 410 to be controlled when the first elongate element 410 is releasably coupled from the second elongate element 412.

The second elongate element 412 may be formed of any material that may hold its shape as it is looped by and coupled to the first elongate element 410. In some instances, the second elongate element 412 may be a wire such as a metal wire or metal rod, a wire thread, or ribbon formed from metal, polymer, or combination thereof.

A transition of the implant release mechanism 402 from the locked and closed configuration to an unlocked and open configuration will be described with respect to FIGS. 4B-4C. In FIG. 4B, the second elongate element 412 (not shown) is retracted proximally from the second elongate element lumen 406 such that the first elongate element 410 is uncoupled from the second elongate element 412, thereby unlocking the implant release mechanism 402. The loop 422 of the first elongate element 410 is no longer coupled to the second elongate element 412 and may move freely out of the second elongate aperture 406. Retraction of the second elongate element 412 also increases slack of the first elongate element 410 and which may permit the channel 420 to be opened. The order of release of the implant release mechanisms 402 begins with the distal-most mechanism and finishes with the most proximal mechanism. The open channel 420 may be configured for passage of a tether coupled to a lumen side of the retaining portion 418.

In FIG. 4C, the first elongate element 410 is retracted proximally to increase tension and/or remove slack in the first elongate element 410. When the first elongate element 410 is retracted 424, the first elongate element 410 is withdrawn into the first elongate element lumen 404 such that the first elongate element 410 is unable to snag against a tissue anchor, heart tissue or any other structure. Retraction of the first and second elongate elements 410, 412 from respective first and second elongate element lumens 404, 406 may be through a first and second elongate element control, as shown in FIG. 2C.

It should be noted that once the second elongate element 412 is retracted, a tether may be released from the outer catheter 400 through the open channel 420 (FIG. 4B) prior to tensioning the first elongate element (FIG. 4C).

FIGS. 5A-5B are perspective views of a distal end of an outer catheter 502. A distal end of the outer catheter 502 may comprise a plurality of tissue anchor apertures 504 separated by a retaining portion 506. The retaining portion 506 as shown in FIG. 5A may include a first elongate element aperture 508 and a first elongate element 510. FIG. 5B illustrates a perspective view of the second elongate element aperture 512 and second elongate element 514. For each retaining portion 506, the first elongate element 510 may extend out of the first elongate element aperture 508, and extend across the retaining portion 506 in a transverse direction with respect to the longitudinal axis of the outer catheter 502. The first elongate element 510 may cross over an external surface of the outer catheter 502 towards the second elongate element aperture 512.

The first elongate element 510 may extend into the second elongate element aperture 512 and loop over the second elongate element 514 to couple the first and second elongate elements 510, 514 to each other. The first elongate element 510 may extend out of the second elongate element aperture 512 and extend back across over the external surface of the outer catheter 502 and over retaining portion 506. The first elongate element 510 may extend into the first elongate element aperture 508. The first elongate element 510 extending between the first and second elongate element apertures 508, 512 (over the retaining portion 506) may cross over or intertwine. In this closed configuration of the retaining portion 506, the first elongate element 510 may be looped around the second elongate element 514 to close the retaining portion 506.

The size and shape of the retaining portions described above are not particularly limited. In some variations, a retaining portion may comprise an aperture having substantially the same width as the tissue anchor aperture such that outer catheter may comprise a single continuous tissue anchor aperture. In these variations, the first elongate element extending across the retaining portion may serve as a physical barrier to secure a portion of a tether to the outer catheter.

In some variations, the first elongate element may extend across the retaining portion at an angle with respect to the longitudinal axis of the outer catheter, for example, in a shoelace pattern. Alternatively, an outer wall structure of the retaining portion and the first elongate element may together physically retain a portion of a tether to the outer catheter until actuation of the implant release mechanism.

In other variations, an implant release mechanism may comprise transverse lumens extending through (i.e., within the thickness of) the retaining portions. A transverse lumen may open into both the first and second elongate element lumens to provide a path for the first elongate element to releasably couple to the second elongate element in the second elongate element lumen. The first elongate element may loop over the second elongate element in a similar manner as described above. In this manner, the first elongate element need not travel over an exterior of the outer catheter to loop and secure to the second elongate element. Furthermore, in these variations, first and second elongate element apertures may be removed such that a distal end of the first and second elongate element lumens are not directly open to fluid and/or tissue within a body cavity such as the heart.

Each retaining portion may comprise at least one transverse lumen. In variations where the retaining portion comprises one transverse lumen, the first elongate element may cross over or intertwine itself within the transverse lumen. In variations where the retaining portion comprises two transverse lumens, the first elongate element may extend through a first transverse lumen, couple to the second elongate element in the second elongate element lumen, and then may extend through a second transverse lumen and back into the first elongate element lumen. In some variations, the transverse lumens need not be perpendicular to the first and second elongate element lumens and may be formed at an angle with respect to the longitudinal axis of the outer catheter. In some instances, the transverse lumens may form an "X" shape to allow the first elongate element to cross over or intertwine itself.

Tissue Anchor

Tissue anchors may be secured to tissue (e.g., the heart) using the outer catheters described to releasably retain a tether coupled to the tissue anchors. "Anchors," as described herein, are defined to mean any fasteners. In some variations, one or more tissue anchors may be loaded into an anchor delivery catheter. An anchor delivery catheter may be advanced through the lumen of an outer catheter described herein and a first tissue anchor may be deployed into heart tissue. The first tissue anchor may be coupled or secured to a tether. The remaining tissue anchors may be slidably coupled to the tether. In some variations, the tether may be in the form of a cable or wire. In this way, after the first tissue anchor is secured to heart tissue, the tether will remain coupled to the first tissue anchor.

While the tether may be used as a track or monorail for the advancement of additional anchor delivery catheters thereover, the tether is also a component of the tissue anchor structure that interconnects the multiple tissue anchors. A portion of the tether may facilitate the tightening of a valve and remain in the body with the tissue anchors after the anchor delivery system is removed from the body. For instance, when pulled proximally while restraining the position of the proximal tissue anchor, the tether may be used to cinch or reduce the circumference of the atrio-ventricular valve annulus or the annular tissue.

Figure 6A:
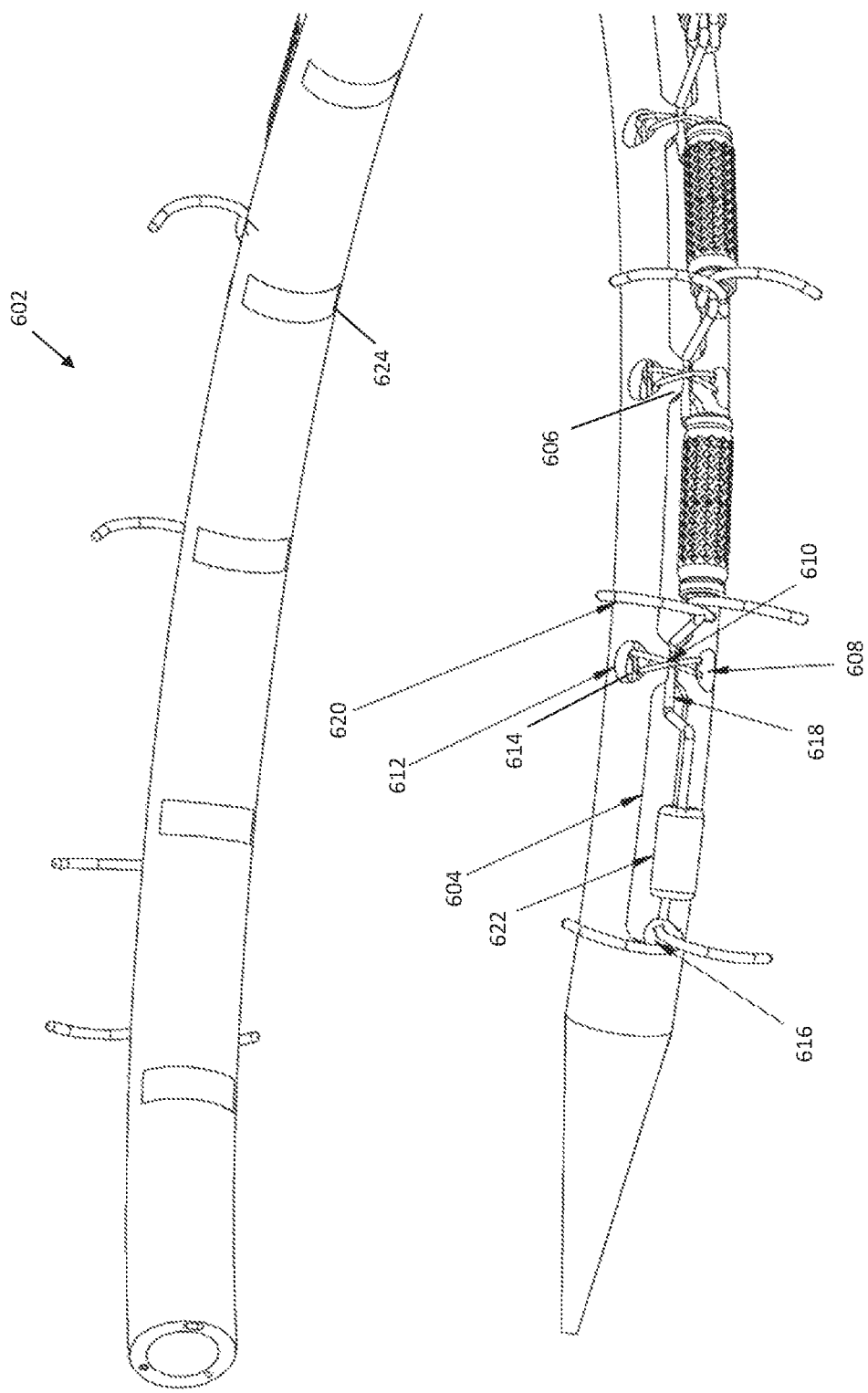
Figure 6B:
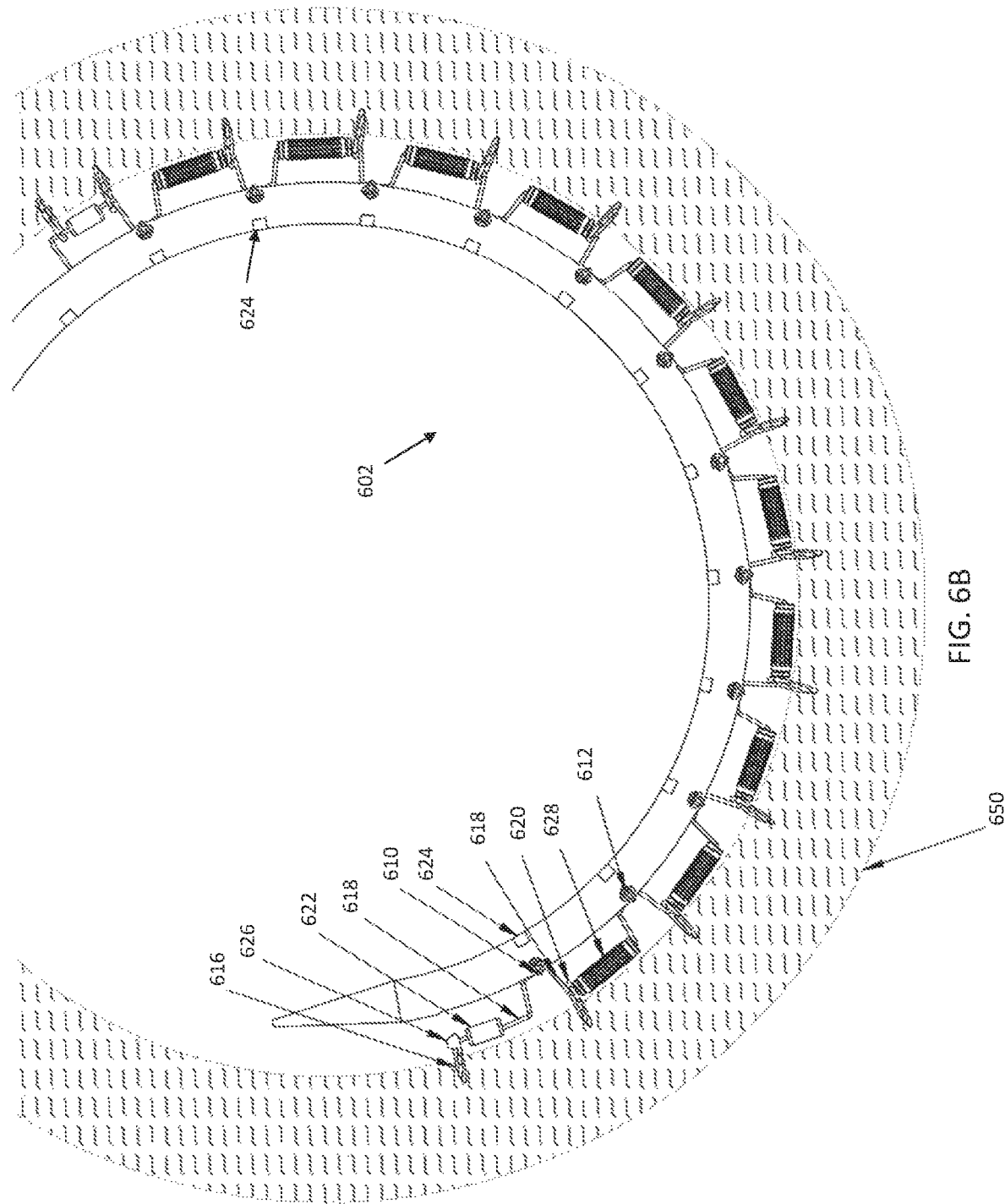
FIG. 6B is a schematic representation of an illustrative variation of a catheter, implant, and heart tissue.

In FIG. 6A, a distal end of outer catheter 602 is depicted and includes a plurality of tissue anchor apertures 604, retaining portions 606, first elongate element apertures 608, second elongate element apertures 612, second elongate element 614, and radiopaque structures 624. For the sake of clarity, heart tissue is not illustrated in FIGS. 6A and 6C-6E. A first tissue anchor 616 is coupled to a second tissue anchor 620 by a tether 618. The tether 618 may be coupled to the first tissue anchor 616 by a knot 626 (FIG. 6B). The attachment of a tissue anchor and tether may be achieved via a knot, weld, adhesive, or by any other suitable attachment mechanism. Optionally, a force distributing member (FDM) or spacer may be provided with varying lengths between tissue anchors. For example, an FDM 622 of a first length may be coupled between the first and second tissue anchors 616, 620, and between the proximal most pair of tissue anchors. An FDM 628 of a second length longer than the first length may be coupled between adjacent intermediate tissue anchors.

The first tissue anchor 616 may be deployed from a tissue anchor lumen through the distal-most tissue anchor aperture 604. The second tissue anchor 620 may be deployed through the next distal-most tissue anchor aperture 604. A portion of the tether 618 is retained on a lumen side of the retaining portion 606. As shown in FIG. 6B, the tether 618 coupled to the first tissue anchor 616 may be slidably coupled to the spacer 626, and may be routed on a lumen side of the retaining portion 606, and then slidably coupled to the spacer 628. This pattern may continue until the most proximal tissue anchor aperture where two tissue anchors are positioned without routing on a lumen side of the retaining portion 616.

As shown in FIG. 6B, each of the tissue anchors may be deployed and secured to heart tissue 650 while the retaining portions 606 are in the closed configuration. At this point, the tissue anchors may be coupled to heart tissue 650 and outer catheter 602. Since the tether 618 is routed on a lumen side of each of the retaining portions 606, the outer catheter 602 cannot be removed from the body without damage to one or more of the heart tissue 650, tissue anchors, and outer catheter 602.

Figure 6C:
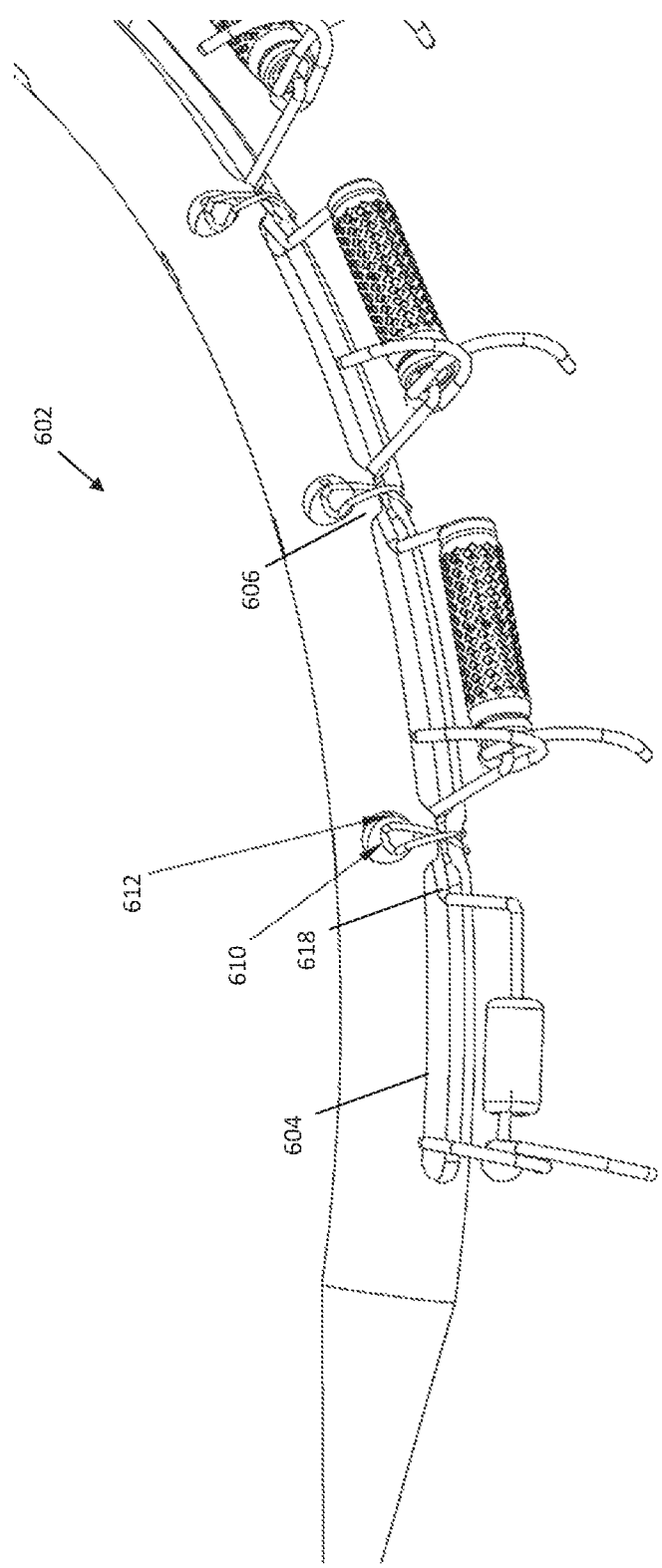
Figure 6E:
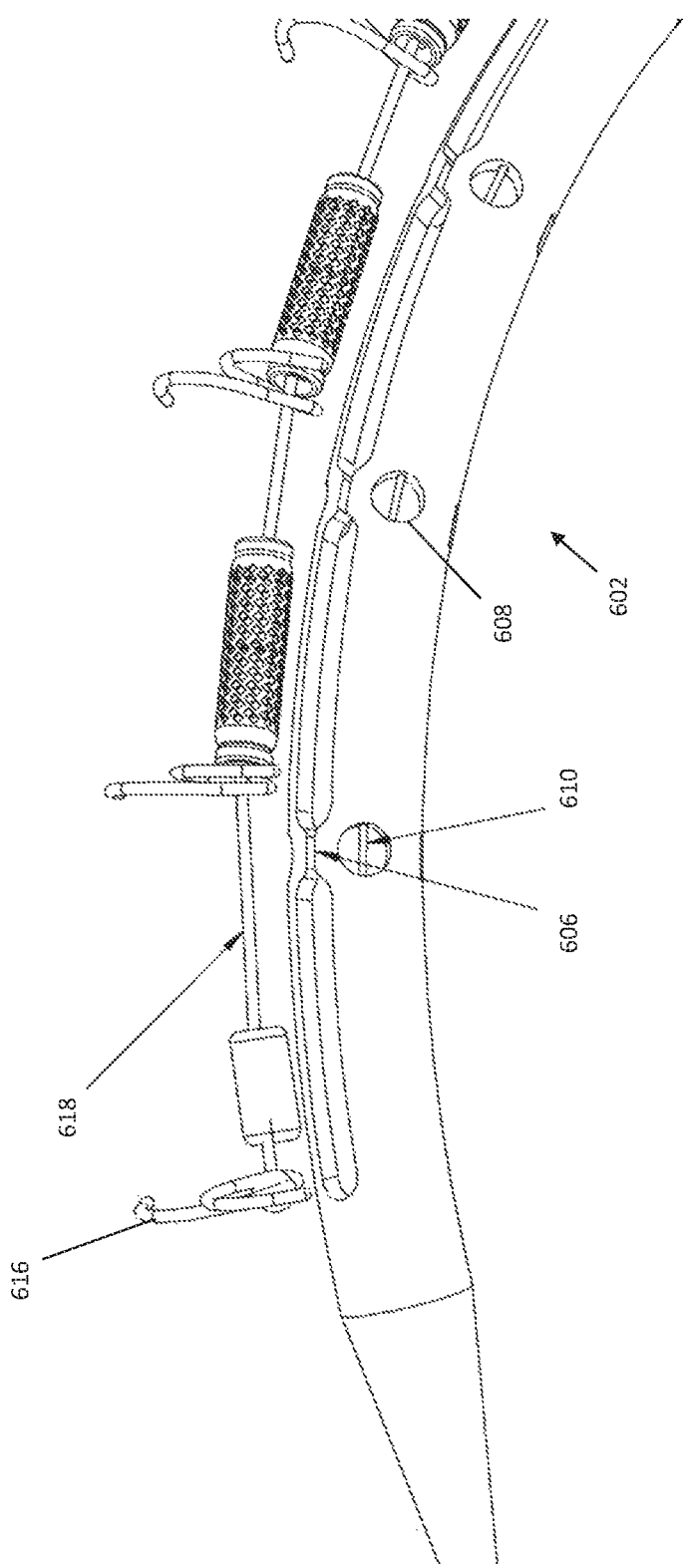

The retaining portions 606 may transition from a closed configuration to an open configuration as explained using FIGS. 6C-6E. FIG. 6C is a perspective view of a distal end of outer catheter 602 after second elongate element (not shown) has been retracted from the second elongate lumen, thus opening the retaining portion 606 and allowing passage of the tether 618 through a channel in the retaining portion 606. For instance, the first elongate element 610 may move freely, as shown in FIG. 6D, and possibly interfere with the tissue anchor or other structures. Therefore, as shown in FIG. 6E, the first elongate element 610 may be retracted and withdrawn into the first elongate element aperture 608. Consequently, the first elongate element 610 does not interfere with any of a tissue anchor 616, tether 618, heart tissue 650, and outer catheter 602 as the outer catheter 602 is separated from the tether 618 and the tissue anchors 616, 620.

In some variations, the tissue anchors may comprise C-shaped or semicircular hooks, curved hooks of other shapes, straight hooks, barbed hooks, clips of any kind, T-tags, or any other suitable fastener(s). In some variations, tissue anchors may comprise two tips that curve in opposite directions upon deployment, forming two intersecting semi-circles, circles, ovals, helices or the like. In some variations, the tips may be sharpened or beveled.

In some variations, the tissue anchors are self-deforming. By "self-deforming" it is meant that the tissue anchors are biased to change from a first undeployed shape to a second deployed shape upon release of the tissue anchors from an outer catheter. Such self-deforming tissue anchors may change shape as they are released from a housing or deployed from a lumen or opening to enter annular tissue, and secure themselves to the tissue. Self-deforming anchors may be made of any suitable material such as spring stainless steel, or super-elastic or shape-memory material like nickel-titanium alloy (e.g., Nitinol). In some variations, anchors may comprise one or more bioactive agents, including biodegradable metals and, polymers.

In some variations, the tether may be made from any suitable or desirable biocompatible material. The tether may be braided or not braided, woven or not woven, reinforced or impregnated with additional materials, or may be made of a single material or a combination of materials. For example, the tether may be made from a suture material (e.g., absorbable suture materials such as polyglycolic acid and polydioxanone, natural fibers such as silk, and artificial fibers such as ultra-high molecular weight polyethylene (UHMW PE), polypropylene, polyester, polyester impregnated with polytetrafluoroethylene, nylon, polyetheretherketone, etc.), a metal (absorbable or non-absorbable), a metal alloy (e.g., stainless steel), a shape memory material, such as a shape memory alloy (e.g., a nickel titanium alloy), other biocompatible material, or any combination thereof.

Hub

A perspective view of the hub 250 is shown in FIG. 2C and may include a first elongate element control port 252, a second elongate element control port 254, an inner catheter port 256, and a guidewire port 258. The control ports 252, 254 may be manipulated to retract and/or withdraw respective first and second elongate elements from their lumens. In one variation, a knob of the control ports 252, 254 may be unscrewed to allow a user to retract at least a portion of the elongate elements out of the control ports 252, 254. In some variations, retracting the first elongate element through the control port 252 may increase the tension of the first elongate element when a distal end of the first elongate element is fixed to a distal end of the outer catheter.

Radiopaque Structures

A radiopaque structure may be located between the plurality of apertures opposite the apertures. The radiopaque structures may be visualized indirectly, such as through fluoroscopy. Accordingly, the radiopaque structures 624 (e.g., FIG. 6B) may facilitate the positioning of a delivery catheter with respect to outer catheter 602. In some variations, the radiopaque structures may be radiopaque markers. Indirect visualization may be utilized throughout the procedures described to confirm catheter positioning relative to heart structures.

II. Methods

The catheters described herein may be useful for detaching or decoupling an outer catheter from an implant. For example, the methods discussed below may allow removal of an outer catheter from a subannular region of the left ventricle of the heart. Generally, removal of an outer catheter may comprise releasing an implant (e.g., tissue anchors) from the outer catheter. The methods may generally involve positioning an outer catheter adjacent to heart tissue, advancing an anchor delivery catheter within the outer catheter, deploying tissue anchors into heart tissue, releasing the tissue anchors from the outer catheter, and removing the outer catheter from the heart. For instance, an implant release mechanism may be actuated to open a passage for release of the tissue anchors, as described in more detail below.

Figure 7A:
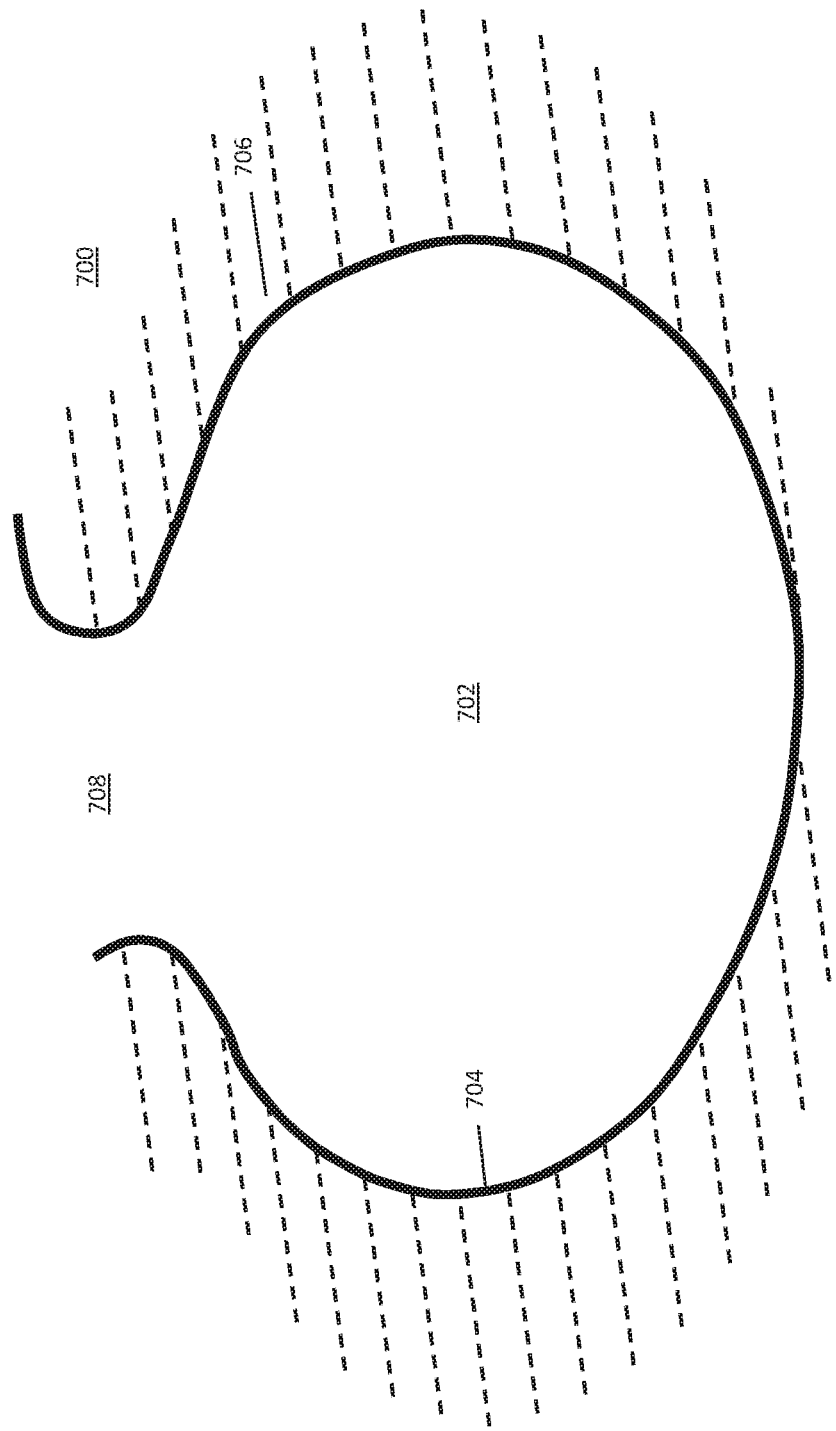
FIGS. 7A-7E are schematic representations of a method for deploying tissue anchors to heart tissue using a catheter.
Figure 7B:
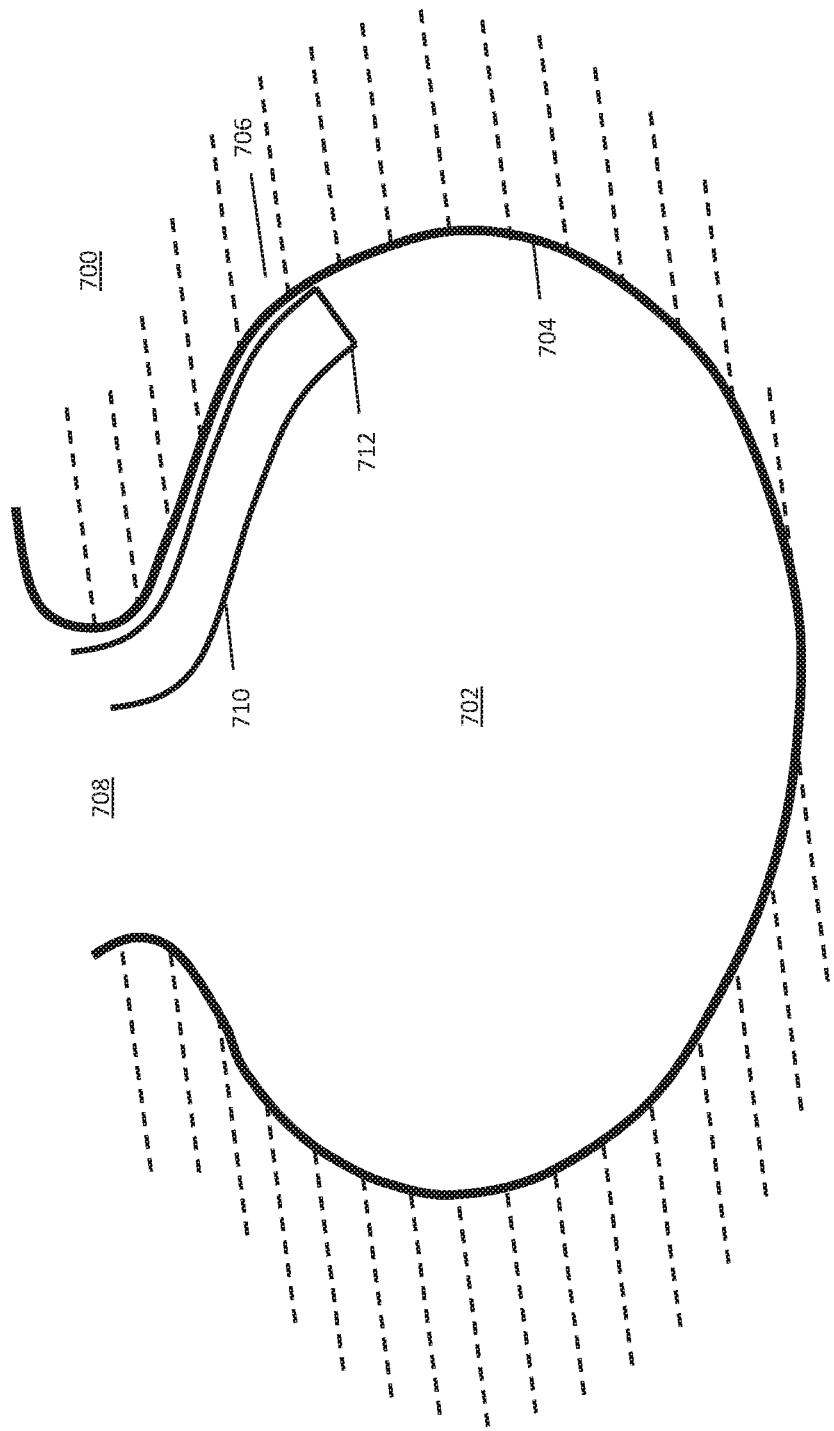
Figure 7C:
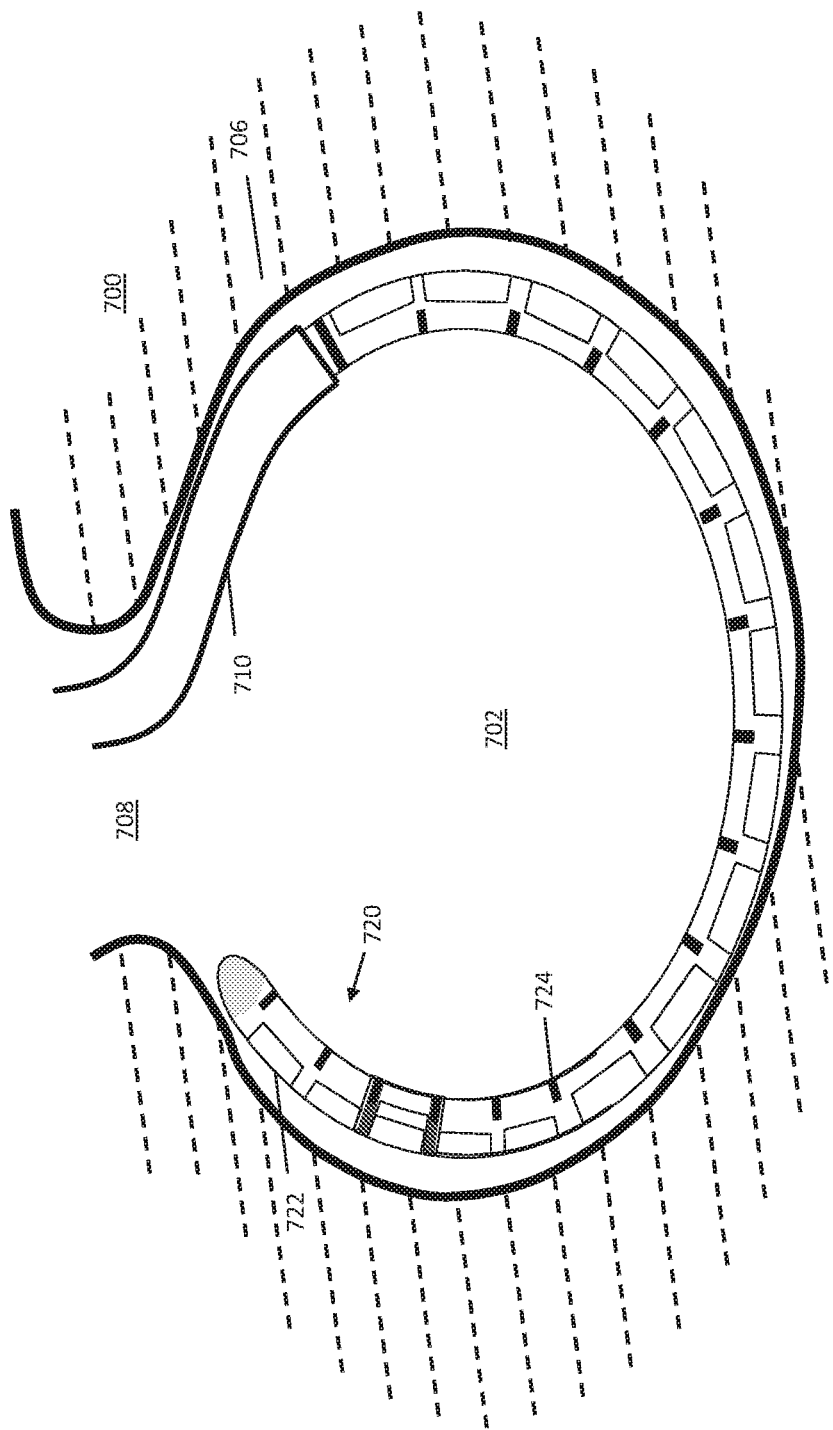
Figure 7D:
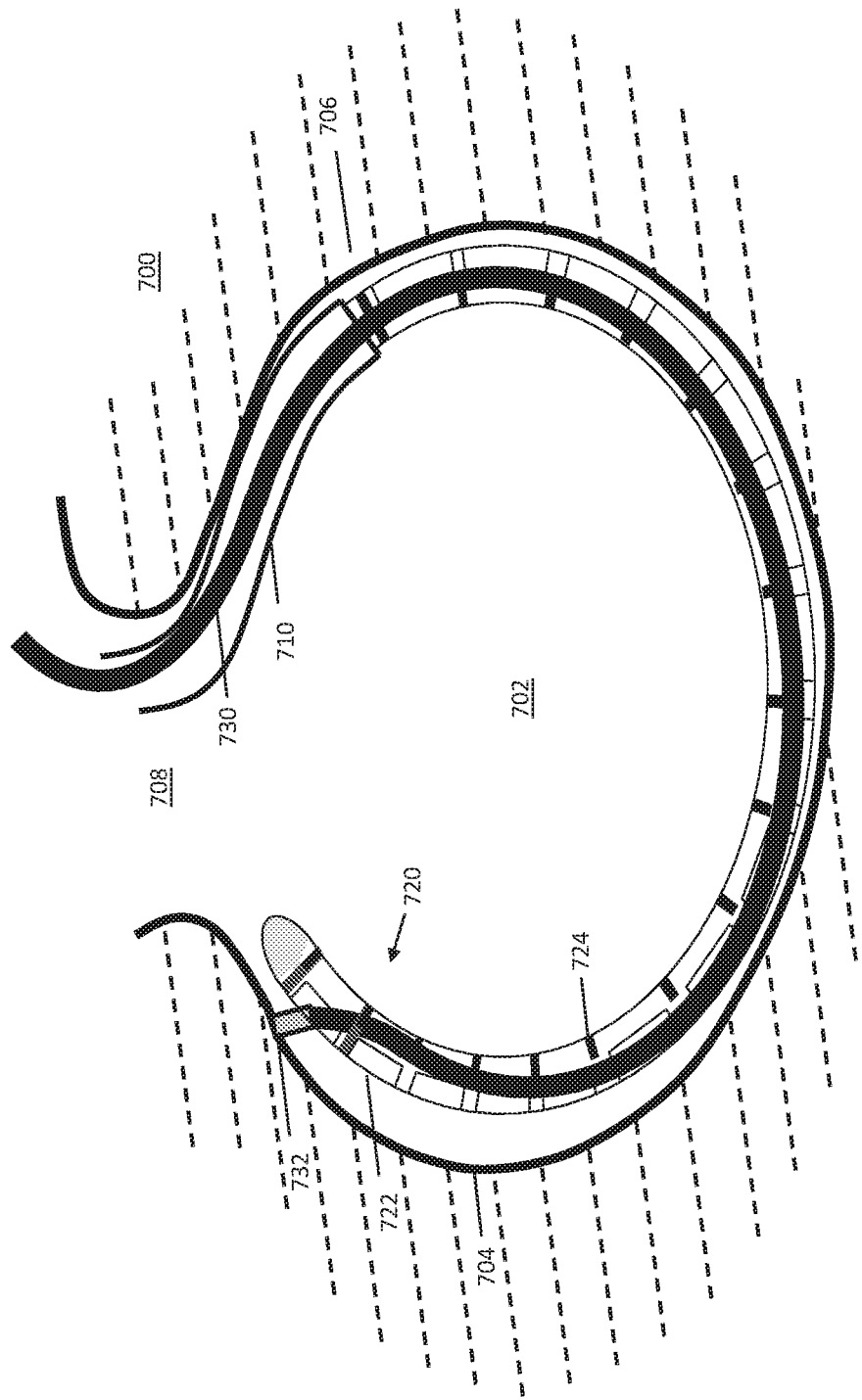
Figure 7E:
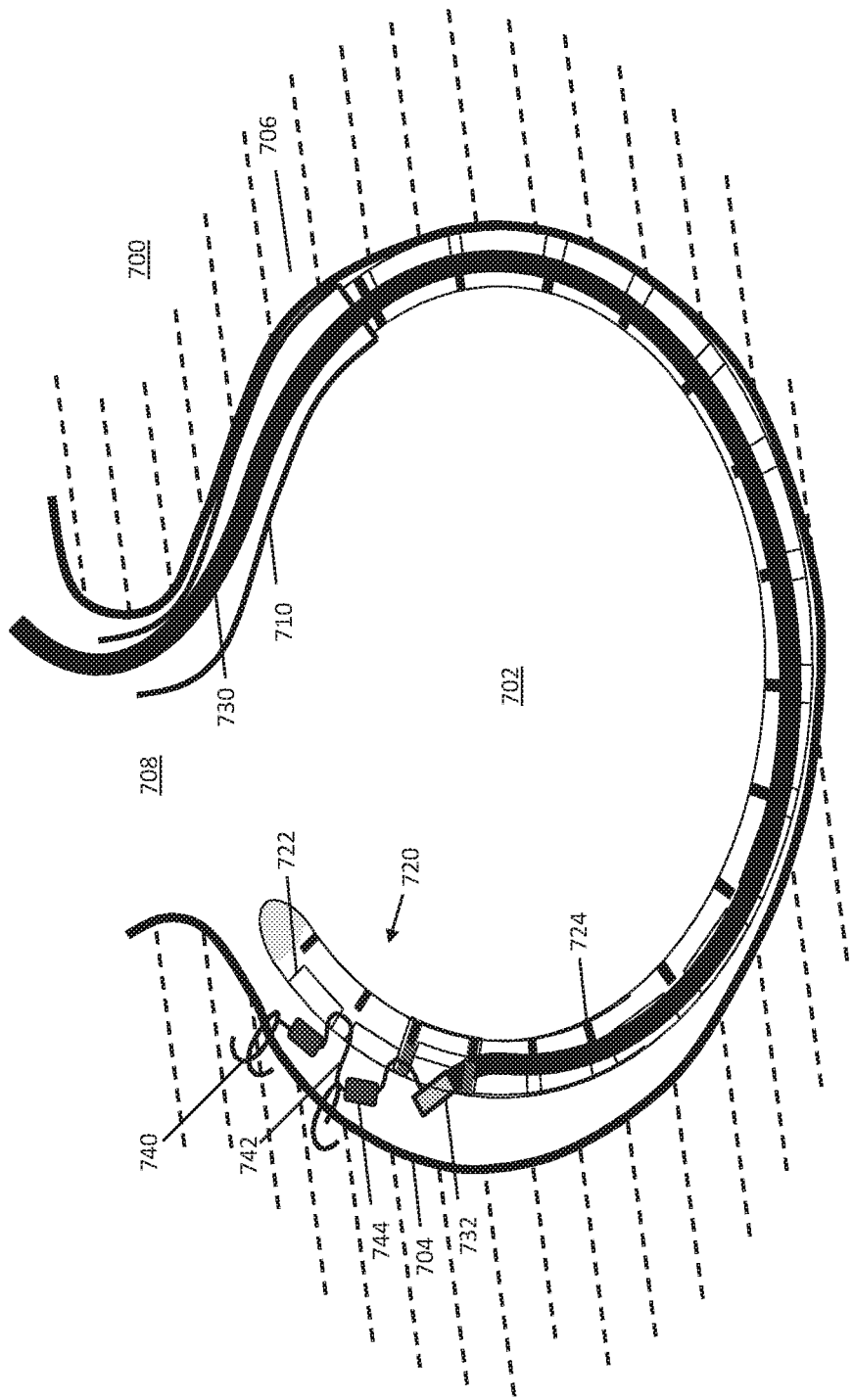
Figure 8:
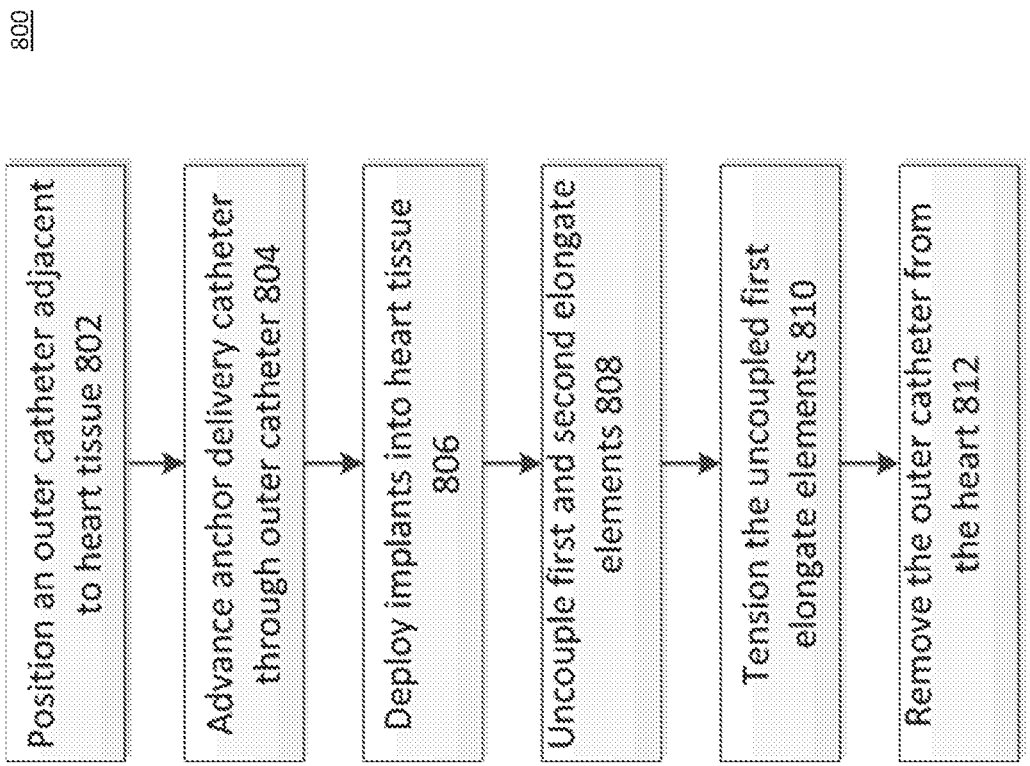
FIG. 8 is a flowchart of an illustrative variation of an implant releasing process.

One variation of a method to detach or decouple an outer catheter from an implant is illustrated in the flowchart 800 of FIG. 8 and may comprise positioning an outer catheter adjacent to heart tissue 802. An inner catheter may be advanced through a lumen of the outer catheter to align with a desired aperture in the outer catheter. An anchor delivery catheter may be advanced through the inner and outer catheter 804. An implant may be deployed into a desired location into heart tissue 806. The implant may comprise a plurality of tissue anchors provided with a predetermined spacing. The implant may further comprise a tether to slidably couple adjacent tissue anchors. First and second elongate elements of an implant release mechanism may be uncoupled 808. For instance, a second elongate element may be retracted from a second elongate element lumen of the outer catheter to uncouple the first elongate element from the second elongate element and thereby open the channel for passage of the implant therethrough. The uncoupled first elongate element 810 may be tensioned to withdraw the first elongate element into the outer catheter. The outer catheter may be removed from the heart 812 with the implant secured to heart tissue. Variations of the methods are further described with respect to FIGS. 7A-7E and 6C-6D.

FIGS. 7A-7E illustrates a heart from an inferior perspective looking in a superior direction for a subannular groove region. FIG. 7A shows a left side of the heart 700 having myocardium 706, endocardium 704, left ventricle (LV) chamber 702, and aortic outflow tract and aortic valve 708. In FIG. 7B, a guide catheter 710 having a distal opening 712 is inserted across the aortic valve 708 and placed tangent to the endocardium 704. After guide catheter 710 has been positioned at the desired location in the subannular groove region, a guidewire (not shown) may be advanced through the lumen of guide catheter 710. The guidewire may be advanced beyond the distal end 712 of guide catheter 710 and positioned in the subannular groove region.

In FIG. 7C, outer catheter 720 may be advanced through guide catheter 710 over the guidewire. The radiopaque structures may be used to position the outer catheter 720 in a desired position to direct placement of tissue anchors into the myocardium 706 of the heart 700. In some variations, outer catheter 720 may be pre-shaped or pre-formed at its distal end to have a curved shape, as illustrated in FIG. 2B. In this manner, the outer catheter 720 may more easily conform to the geometry of the atrio-ventricular valve. It should also be understood that any of the catheters or guidewires described here may be pre-shaped or pre-formed to include any number of suitable curves, angles or configurations. The guidewires and/or catheters described here may also be steerable.

Once the outer catheter 720 is positioned against or near the endocardium 704 through the guide catheter 710, the guidewire may be withdrawn proximally and the outer catheter 720 may direct the placement of an implant, such as heart tissue anchors, into myocardium 706 of the left ventricle 702. For instance, the tissue anchors may be deployed to a depth of about 6 mm. The outer catheter 720 may comprise a plurality of tissue anchor apertures 722 and radiopaque structures 724. The outer catheter 720 may be indirectly visualized through the radiopaque structures 724.

As shown in FIG. 7D, an anchor delivery catheter 730 may be advanced through the lumen of outer catheter 720 such that a distal tip 732 of the anchor delivery catheter 730 may exit a tissue anchor aperture 722 and contact the endocardium 704. Further advancement of the delivery catheter 730 may cause the distal tip 732 to penetrate the endocardium 704 to a desired depth. In some variations, the anchor delivery catheter 730 remains within outer catheter 720, while a tissue anchor is deployed through the tissue anchor aperture 722.

FIG. 7E depicts tissue anchors 740 being deployed and secured into endocardium 704. A first tissue anchor completed to a tether 742 may be deployed into the myocardium 706 at a predetermined depth from a first tissue anchor aperture 722. The anchor delivery catheter 730 may then be withdrawn proximally from the outer catheter 720. While maintaining the existing position of the outer catheter 720 about the subannular groove region, an inner catheter (not shown) of the outer catheter 720 may be repositioned at the second distal-most tissue anchor aperture 722.

A second anchor delivery catheter 730 may then be advanced over the tether 742 through the lumen of the catheter 730. After the second anchor delivery catheter 730 has been advanced over the tether 742 through the lumen of the outer catheter 720, a second tissue anchor 744 may be deployed into the myocardium 706 from a second tissue anchor aperture 722. This process may continue for each of the tissue anchor apertures 722 of outer catheter 720.

FIG. 7E illustrates the anchor delivery catheter 730 extending out of a third tissue anchor aperture 722 prior to deploying a third tissue anchor. It should be noted that the tether 742 may be routed into a tissue anchor lumen of the outer catheter 720 between adjacent tissue anchor apertures 722. As the delivery catheter 730 deploys the tissue anchors 740 into the myocardium 706, the tether 742 may be retained by an implant release mechanism provided between adjacent tissue anchor apertures, thereby temporarily securing the outer catheter 720 to the heart 700 and maintaining its location with respect to the heart. In other words, the process of delivering tissue anchors into heart tissue may also indirectly attach the outer catheter 720 to the heart tissue due to the tether 742 being routed on a lumen side of the outer catheter 720 between adjacent tissue anchor apertures 722.

In some variations, delivery and deployment of tissue anchors may be achieved by removing and reloading the same anchor delivery catheter 730. In other variations, the anchor delivery catheter may be loaded with a plurality of tissue anchors and does not need to be withdrawn from the outer catheter 720 to deliver subsequent tissue anchors.

It should be appreciated that one or more tissue anchors 740 may be deployed into the annulus directly, while other tissue anchors may be secured to other tissue in the vicinity of the subannular groove region. Tissue anchors 740 may be deployed from the anchor delivery catheter 730 and outer catheter 720 in any suitable fashion, including but not limited to a push-pull wire, using a plunger, or other suitable actuation technique.

Turning back to FIGS. 6C-6D, a second elongate element may be retracted proximally from the second elongate lumen of outer catheter 602 to uncouple the first elongate element 610 from the second elongate element and increase the slack of the first elongate element 610. A channel of the implant release mechanism (e.g., retaining portion 606) is thus opened for passage of the tether 618 between the first and second tissue anchor apertures 604.

Once the second elongate element is retracted, the uncoupled first elongate element 610 may be tensioned to withdraw the first elongate element 610 into the first elongate element lumen of the outer catheter 602, as shown in FIG. 6E, thereby preventing the first elongate element 610 from snagging or interfering with the tissue anchors 616, tether 618, outer catheter 602, and heart tissue 650. The tether 618 is fully free to come out of and separate from the outer catheter 602 to allow the outer catheter 602 to be withdrawn and removed from the heart. In some variations, as the outer catheter is removed from the heart, the tether 618 may pass through a channel of the retaining portion 606. In some variations, the tether 618 may be tensioned to help release and/or separate the tether from the outer catheter without disrupting the implanted anchors.

It should be noted that prior to introducing the outer catheter into a body cavity, the first elongate element may be crossed over itself and coupled to a second elongate element, as shown in FIG. 5B. In this manner, the first elongate element is tensioned against the second elongate element to close a channel of a retaining portion.

The procedures described above represents variations that may be used to treat the annular tissue of the mitral valve. In other variations, other tissues or structures of the heart and vasculature can also be treated, including but not limited to the subvalvular apparatus, septal structures, and the myocardium. In still other variations, one or more cinchable implants may be deployed in non-cardiac tissues or structures, for example, to treat gastrointestinal disorders such as obesity, genitourinary conditions such as incontinence, or to perform cosmetic and reconstructive procedures.

While the inventive devices, systems, and methods have been described in some detail by way of illustration, such illustration is for purposes of clarity of understanding only. It will be readily apparent to those of ordinary skill in the art in light of the teachings herein that certain changes and modifications may be made thereto without departing from the spirit and scope of the appended claims.

We claim:

1. An implant delivery system comprising:
a catheter comprising a longitudinal axis, a first elongate element lumen, a second elongate element lumen, a tissue anchor lumen, and a plurality of apertures along the longitudinal axis, wherein the plurality of apertures comprise first elongate element apertures, second elongate element apertures, and tissue anchor apertures, wherein the catheter comprises a plurality of retaining portions each between adjacent tissue anchor apertures and between adjacent first and second elongate element apertures;
a first elongate element within the first elongate element lumen; and
a second elongate element within the second elongate element lumen, wherein for each pair of adjacent first and second elongate element apertures, the first elongate element extends out of the first elongate element lumen through the first elongate element aperture across the retaining portion transversely with respect to the longitudinal axis and towards the second elongate element aperture, and the first elongate element extends into the second elongate element aperture, loops over the second elongate element, and extends back across the retaining portion and into the first elongate element lumen.

2. The implant delivery system of claim 1, wherein the first elongate element is releasably coupled to the second elongate element.

3. The implant delivery system of claim 1, wherein the first elongate element extending between the first and second elongate element apertures crosses over itself.

4. The implant delivery apparatus of claim 1, wherein the first elongate element is fixed to a distal end of the catheter.

5. The implant delivery system of claim 1, further comprising a first elongate element control configured to retract the first elongate element from the first elongate element lumen and a second elongate element control configured to retract the second elongate element from the second elongate element lumen.

6. The implant delivery system of claim 5, wherein retracting the first elongate element from the first elongate element lumen tensions the first elongate element.

7. The implant delivery system of claim 1, wherein the plurality of retaining portions each comprise a channel along the longitudinal axis.

8. The implant delivery system of claim 7, wherein the plurality of retaining portions are each adapted to open the channel.

9. The implant delivery system of claim 1, further comprising at least one radiopaque structure located between the plurality of apertures.

10. The implant delivery system of claim 1, further comprising an anchor delivery catheter advanceable within the catheter and a plurality of tissue anchors within the anchor delivery catheter.

11. The implant delivery system of claim 10, wherein the tissue anchor apertures are configured for passage of the plurality of tissue anchors.

12. The implant delivery system of claim 10, wherein the anchor delivery catheter is advanceable within the tissue anchor lumen.

13. A method for performing a procedure inside a heart comprising:

positioning a catheter adjacent to heart tissue, wherein the catheter comprises a longitudinal axis, a first elongate element lumen, a second elongate element lumen, a tissue anchor lumen, and a plurality of apertures along the longitudinal axis, wherein the plurality of apertures comprise first elongate element apertures, second elongate element apertures, and tissue anchor apertures, the catheter further comprising a plurality of retaining portions each between adjacent tissue anchor apertures and between adjacent first and second elongate element apertures, a first elongate element within the first elongate element lumen and a second elongate element within the second elongate element lumen, wherein the plurality of retaining portions each comprise a channel along the longitudinal axis, wherein for each pair of adjacent first and second elongate element apertures, the first elongate element extends out of the first elongate element lumen through the first elongate element aperture across the retaining portion transversely with respect to the longitudinal axis and towards the second elongate element aperture, and the first elongate element extends into the second elongate element aperture, loops over the second elongate element, and extends back across the retaining portion and into the first elongate element lumen;

deploying a first tissue anchor and at least a second tissue anchor into the heart tissue, wherein a tether couples the first tissue anchor to at least the second tissue anchor;

retracting the second elongate element from the second elongate element lumen to uncouple the first elongate element from the second elongate element and to open the channel for passage of the first and second tissue anchors;

tensioning the uncoupled first elongate element;

removing the catheter from the heart.

14. The method of claim 13 wherein the catheter is temporarily secured to heart tissue using at least one of the first and second tissue anchor.

15. The method of claim 13 wherein retracting the second elongate element increases slack of the first elongate element.

16. The method of claim 13 wherein retracting the second elongate element opens the channel.

17. The method of claim 13 further comprising crossing the first elongate element over itself.

18. The method of claim 13 further comprising tensioning the first elongate element against the second elongate element.

19. The method of claim 13 further comprising advancing an anchor delivery catheter within the catheter.

* * * * *